US007892835B2

(12) United States Patent
Akaike et al.

(10) Patent No.: US 7,892,835 B2
(45) Date of Patent: Feb. 22, 2011

(54) PLURIPOTENT STEM CELL GROWING METHOD

(75) Inventors: Toshihiro Akaike, Tokyo (JP); Keiichi Fukuda, Tokyo (JP); Masato Nagaoka, Kanagawa (JP); Uichi Koshimizu, Osaka (JP)

(73) Assignee: Daiichi Sankyo Company, Limited, Chuo-Ku, Tokyo (JP)

( * ) Notice: Subject to any disclaimer, the term of this patent is extended or adjusted under 35 U.S.C. 154(b) by 481 days.

(21) Appl. No.: 10/593,831

(22) PCT Filed: Mar. 23, 2005

(86) PCT No.: PCT/JP2005/006006

§ 371 (c)(1),
(2), (4) Date: Sep. 22, 2006

(87) PCT Pub. No.: WO2005/090557

PCT Pub. Date: Sep. 29, 2005

(65) Prior Publication Data

US 2007/0155013 A1  Jul. 5, 2007

(30) Foreign Application Priority Data

Mar. 23, 2004  (JP) ............................ 2004-085393

(51) Int. Cl.
*C12N 15/09* (2006.01)
*C12N 5/06* (2006.01)
*C12N 5/08* (2006.01)

(52) U.S. Cl. ......................... 435/455; 435/354; 435/366
(58) Field of Classification Search ........................ None
See application file for complete search history.

(56) References Cited

FOREIGN PATENT DOCUMENTS

| JP | 2001061470 A | 3/2001 |
|---|---|---|
| WO | WO 01/51616 | 7/2001 |
| WO | WO 01/66697 A2 | 9/2001 |
| WO | WO 03/020920 A1 | 3/2003 |
| WO | WO 03/087305 | 10/2003 |

OTHER PUBLICATIONS

Nagaoka et al (Biotechnology Letters, 2002; 24: 1857-1862).*
Nicolas et al, (Ann. Microbiol. Paris., 126: 3-22, 1975).*
Alonso et al. (Int. J. Dev. Biol. 1991; 389-397).*
Xu et al. (Nature Biotechnology. Oct. 2001; 19: 971-974).*
Song et al. (PNAS. Nov. 12, 2002; 99(23): 14813-14818).*
Fuchs et al. (Cell. Mar. 19, 2004; 116: 769-778).*
Hurt et al. (Cancer Cell. Feb 2004; 5: 191-199).*
Giesberts et al. (Mechanisms of Development. 1999; 83: 115-125).*
Kovacs, et al., "Cadherin-Directed Actin Assembly: E-Cadherin Physically Associates with the Arp2/3 Complex to Direct Actin Assembly in Nascent Adhesive Contacts", Current Biology, vol. 12, p. 379-382, Mar. 5, 2002.

Nagaoka, et al., "E-Cadherin-Coated Plates Maintain Pluripotent ES Cells without Colony Formation", PloS One, Issue 1, e15, p. 1-7, Dec. 2006.
Alonso, et al. (1991) "The F9-EC cell line as a model for the analysis of differentiation." Int. J. Dev. Biol. 35: 389-397.
Andrews (2002) "From teratocarcinomas to embryonic stem cells." Phil. Trans. R Soc. Lond. 957: 405-417.
Artzt, et al. (1973) "Surface Antigens Common to Mouse Cleavage Embryos and Primitive Teratocarcinoma Cells in Culture." Proc. Nat. Acad. Sci. USA 70(10): 2988-2992.
ATCC Information on F9 Teratocarcinoma Cells (Catalog # ) [downloaded from ATCC.org on Apr. 20, 2010].
Avner, et al. (1978) "The Genetics of Teratocarcinoma Transplatation: Tumor Formation in Allogeneic Hosts by the Embryonal Carcinoma Cell Lines F9 and PCC3." Immunogenetics 7: 103-115.
Nicolas, et al. (1975) Annales de Microbiologie 126(1): 3-22.
Painter (1928) "A Comparison of the Chromosomes of the Rat and Mouse with Reference to the Question of Chromosome Homology in Mammals." Genetics 13: 180-189.
M. Nagaoka, et al., "Analysis of the E-cadherin function of Undifferentiated Cells by Immobilized E-cadherin Model Protein", Cell Structure and Function, vol. 28, No. 4, p. 327, IP-53, 2003.
M. Nagaoka, et al., "E-cadherin/IgG Fc Yugo Tanpakushitsu Ni Yoru Saibo Setchaku Kino No Seigyo to Saisei Ikogaku Eno Oyo", Bio. Kobunshi Symposium Koen Yoshishu, vol. 13th, pp. 31-32, 2003.
M. Nagaoka, et al., "Saisei Iryo Zairyo to Shite No E-cadherin Model Bunshi No Soshiki Saikochiku Eno Oyo", The Japanese Society for Regenerative Medicine Zasshi, vol. 1, No. 1, p. 83, Abstract No. 63, 2002.
M. Amit, et al., "Clonally Derived Human Embryonic Stem Cell Lines Maintain Pluripotency and Proliferative Potential for Prolonged Periods of Culture", Dev. Biol., vol. 227, No. 2, pp. 271-278, 2000.
M. Nagaoka, et al., "Bio Material to Tissue Engineering Matrix Kogaku Ni Yoru Kansaibo No Bunka Zoshoku Seigyo", Saisei Iryo, vol. 3, No. 2, pp. 47-54, (2005).
M. Nagaoka, et al., "E-cadherin Model Tanpakushitsu o Mochiita ES Saibo No Kokoritsu Baiyoho No Kakuritsu", Dai 27 Kai The Molecular Biology Society of Japan Nenkai Program Koen Yoshishu, p. 758, 2PB-224, Nov. 25, 2004.

* cited by examiner

*Primary Examiner*—Scott Long
(74) *Attorney, Agent, or Firm*—Hunton & Williams LLP

(57) ABSTRACT

A novel growing method is provided for pluripotent stem cells such as ES cells. The method of the invention is a pluripotent stem cell growing method and gene transfer method in which pluripotent stem cells are cultured under conditions that maintain their undifferentiated state and pluripotency, the method being characterized by using a liquid medium and a culturing vessel having immobilized or coated on a substrate solid phase surface a molecule which is adhesive to the pluripotent stem cells in a fixed concentration, to grow the pluripotent stem cells in a dispersed state while maintaining their undifferentiated state and pluripotency, without using feeder cells, or to transfer and express a gene therein.

13 Claims, 12 Drawing Sheets

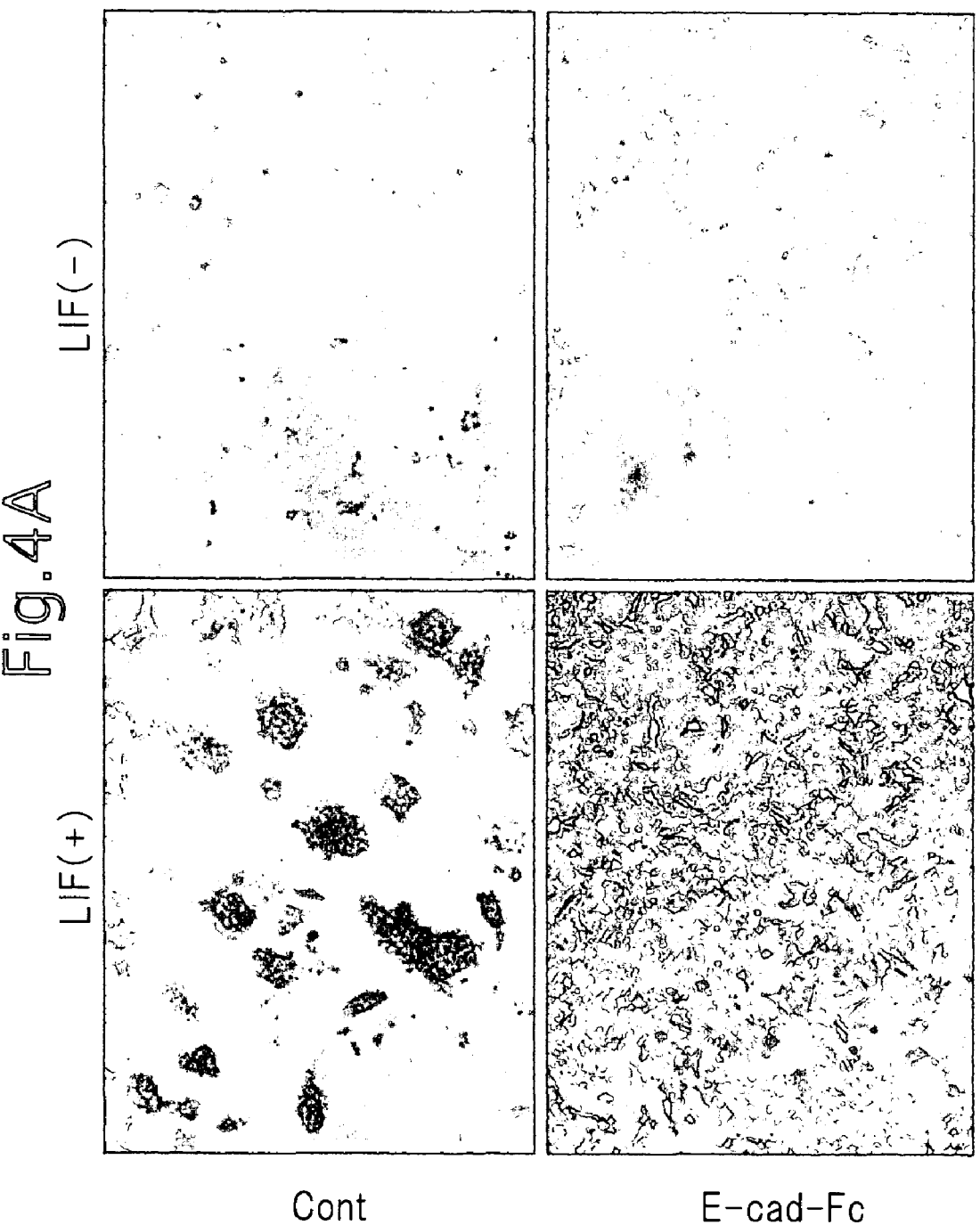

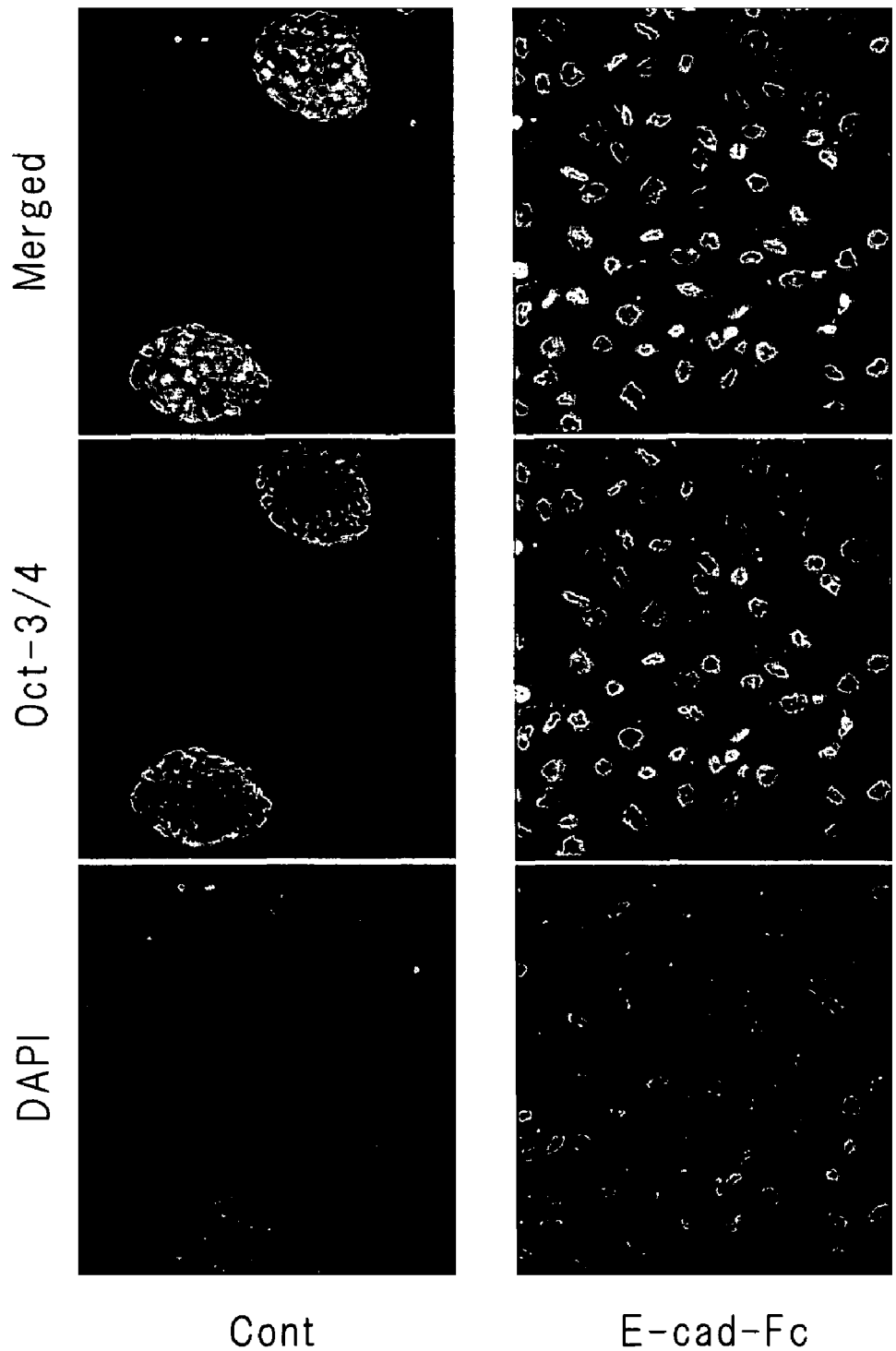

Fig.8
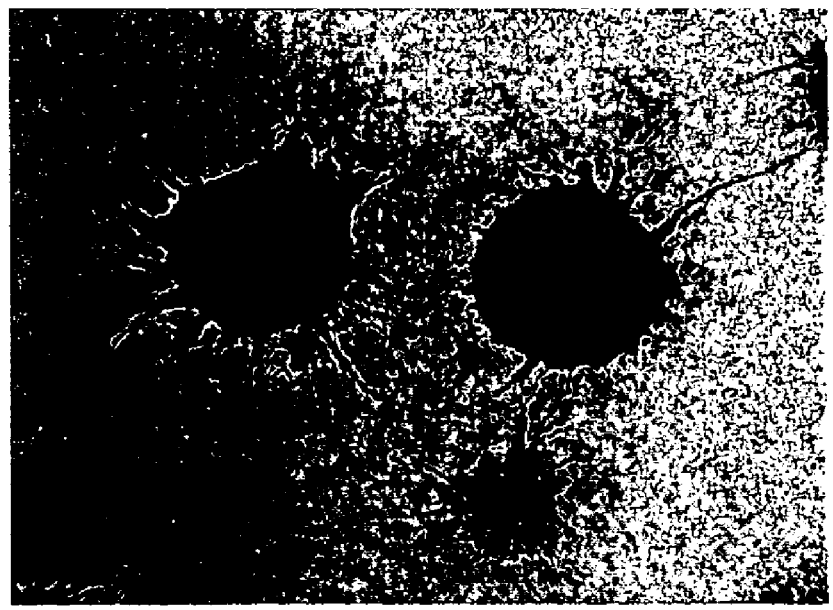
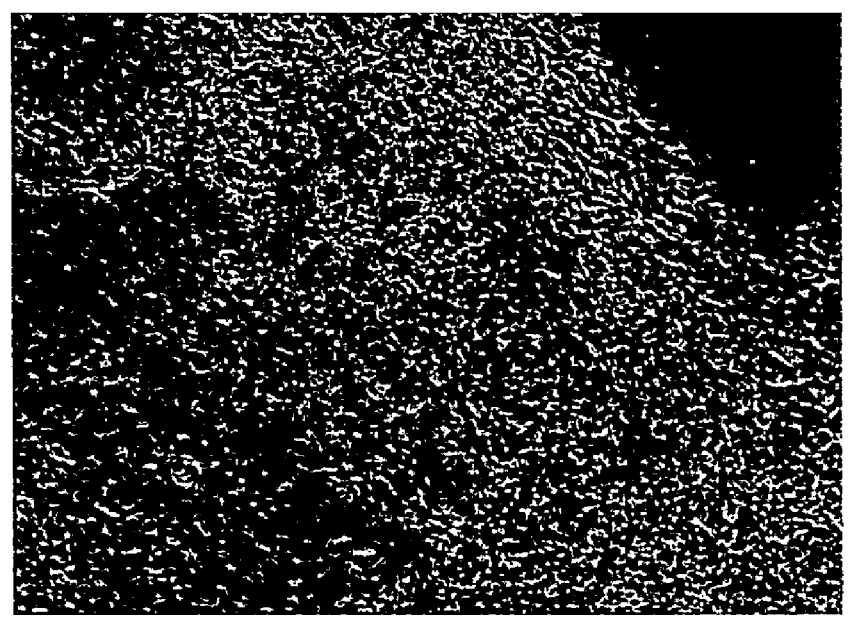

PLURIPOTENT STEM CELL GROWING METHOD

CROSS-REFERENCE TO RELATED APPLICATIONS

This application is the U.S. National Stage Application of International Application No. PCT/JP2005/006006, filed on Mar. 23, 2005, which claims the benefit of Japanese Patent Application No. 2004-085393, filed on Mar. 23, 2004, the disclosures of each of which are herein incorporated by reference in their entireties.

BACKGROUND OF THE INVENTION (i) Field of the Invention

The present invention relates to a growing method and to a gene transfer method for pluripotent stem cells such as ES cells, and to pluripotent stem cells prepared by the methods.

(ii) Description of the Related Art

In order to continue to live, organisms have the ability to rapidly replace and repair lost or damaged cells and tissue, and this ability is known as "regenerative capacity". Examples of "regenerative capacity" in higher animals include the commonly known phenomena of wound healing of skin and blood vessels, but even parenchymal organs such as the liver and kidneys are known to undergo cell growth and tissue reconstruction for rapid restoration of tissue homeostasis in response to tissue damage. Recent years have seen attempts to utilize this innate "regenerative capacity" of biological organisms to achieve cures or amelioration of various diseases and wounds, and such new medical techniques are coming to be known as "regenerative medicine".

Stem cells play a central role in practicing "regenerative medicine". "Stem cells" can be generally defined as undifferentiated cells having the ability to differentiate into specialized cells or polyfunctional cells, as well as having the ability to self-replicate, allowing repeated generation of cells identical to themselves. Unique stem cells are found in each tissue and cell type, and for example, blood cells such as erythrocytes, lymphocytes and megakaryocytes are produced via progenitor cells derived from stem cells known as "hematopoietic stem cells", while skeletal muscle cells are produced from stem cells/precursor cells known as "satellite cells" and "myoblasts". Additional types that have been identified to date include neural stem cells that are found in neural tissue such as the brain and spinal cord and produce neurons and glial cells, epidermal stem cells that produce epidermal cells and hair follicle cells, oval cells (hepatic stem cells) that produce hepatocytes and bile duct cells, and cardiac stem cells that produce cardiomyocytes.

Some regenerative medicine treatments using stem cells or precursor cells derived from such cells have already been implemented, and infusion graft methods with hematopoietic stem cells or hematopoietic precursor cells are well known for treatment of conditions caused by a lack or functional deficiency of blood cells, such as leukemia and aplastic anemia. However, stem cells present in parenchymal organs such as the brain, heart or liver are technically difficult to obtain from living tissues and/or to culture in vitro, and such stem cells also generally have low proliferation potency. Stem cells can also be recovered from tissues from corpses, but the medical use of cells obtained in this manner is associated with ethical problems. Consequently, regenerative treatments for neuropathy, cardiopathy and the like will require the development of techniques for generating desired cell types using cells other than stem cells present in such target tissues.

First, methods of utilizing "pluripotent stem cells" may be mentioned as strategies based on this approach. "Pluripotent stem cells" are defined as cells capable of prolonged or virtually indefinite proliferation in vitro while retaining their undifferentiated state, exhibiting normal karyotype (chromosomes) and having the capacity to differentiate into all cell types of the three germ layers (ectoderm, mesoderm and endoderm) under the appropriate conditions. Currently the most commonly known pluripotent stem cells are embryonic stem cells (ES cells) isolated from the early embryo, and the analogous embryonic germ cells (EG cells) isolated from fetal primordial germ cells, both of which are the subjects of ongoing research.

ES cells can be isolated as an undifferentiated stem cell population by transferring the inner cell mass of a blastocyst-stage embryo to in vitro culture and repeating the process of detaching and passaging the cell mass. The cells have suitable cell density on feeder cells prepared from primary cultured murine embryonic fibroblasts (hereinafter, MEF cells) derived from murine fetal tissue or stromal cells such as STO cells, and repeated passaging with frequent replacement of the culture medium can lead to establishment of a cell line retaining the property of undifferentiated stem cells. Another feature of ES cells is the presence of the enzyme telomerase, which exhibits an activity of maintaining chromosomal telomere length, and this enzyme confers to ES cells the capacity for virtually unlimited cell division in vitro.

ES cell lines produced in this manner are "pluripotent" as they can be repeatedly grown and passaged almost indefinitely while maintaining normal karyotype, and they are capable of differentiating into various different cell types. For example, when ES cells are transplanted into an animal body subcutaneously, intraabdominally or intratesticularly they form tumors called "teratomas", but the tumors comprise a mixture of different cells and tissues including neurons, osteocytes, chondrocytes, intestinal cells, muscle cells and the like. In mice, intrauterine transplantation into a pseudopregnant mouse of an aggregate embryo generated by infusion graft of ES cells into a blastocyst-stage embryo or aggregation with an eight-cell stage embryo, results in generation of a "chimeric mouse", which is an offspring possessing differentiated cells derived from the ES cells throughout the entire body or in parts of its organs and tissues. This technique is often used as a main method for generating "knockout mice" having certain genes which are artificially disrupted or modified.

It is also well known that ES cells are induced to differentiate into diverse types of cells by in vitro culturing as well. While the specific method differs depending on the type of cell, it is common to employ a method of inducing differentiation by forming an "embryoid body" (hereinafter, "EB") which is a cell mass in an embryo-like state produced by aggregating ES cells by suspension culture. Such a method can produce cells having fetal stage endoderm, ectoderm and mesoderm characteristics, as well as differentiated cells such as blood cells, vascular endothelial cells, chondrocytes, skeletal muscle cells, smooth muscle cells, cardiomyocytes, glial cells, neurons, epithelial cells, melanocytes, keratinocytes, adipocytes and the like. Differentiated cells produced by in vitro culturing in this fashion have essentially the same structural and functional features as cells present in organs and tissues, and transplant experiments using experimental animals have demonstrated that ES cell-derived cells anchor to organs and tissues and function normally.

For reviews of ES cell properties and culturing methods, and their in vivo and in vitro differentiating abilities, refer to the following literature: Guide to Techniques in Mouse Development (Wasserman et al., Academic Press, 1993); Embryonic Stem Cell Differentiation in vitro (M. V. Wiles, Meth. Enzymol. 225:900, 1993); Manipulating the Mouse Embryo: *A Laboratory Manual* (Hogan et al., Cold Spring Harbor Laboratory Press, 1994)(Non-patent document 1); Embryonic Stem Cells (Turksen, ed., Humana Press, 2002) (Non-patent document 2).

EG cells can be produced by stimulating fetal germ cells known as primordial germ cells on feeder cells such as MEF cells or STO cells in the same manner as ES cells, using Leukemia Inhibitory Factor (hereinafter, LIF) and basic Fibroblast Growth Factor (hereinafter, bFGF/FGF-2), or chemical agents such as forskolin (Matsui et al., Cell 70:841, 1992; Koshimizu et al., Development 122:1235, 1996). It has been confirmed that EG cells have properties very similar to ES cells and have pluripotency (Thomson & Odorico, Trends Biotechnol. 18:53, 2000). Throughout the present specification, therefore, the term "ES cells" may include "EG cells".

After Thomson et al. first established ES cells from a primate (rhesus monkey) in 1995, the concept of regenerative medicine using pluripotent stem cells began to approach the realm of possibility (U.S. Pat. No. 5,843,780; Proc. Natl. Acad. Sci. USA 92:7844, 1995). Later, the researchers used similar methods to successfully isolate and establish ES cell lines from human early embryos (Science 282:114, 1998). Research groups in Australia and Singapore later submitted similar reports (Reubinoff et al., Nat. Biotech. 18:399, 2000; International Patent Publication No. WO00/27995), and currently 20 different human ES cell lines have been registered at the U.S. National Institutes of Health (NIH) (http://stemcells.nih.gov/registry/index). Also, Gearhart and their colleagues have succeeded in establishing a human EG cell line from human primordial germ cells (Shamblott et al., Proc. Natl. Acad. Sci. USA 95:13726, 1998; U.S. Pat. No. 6,090,622).

When these pluripotent stem cells are used to produce research materials or regenerative medicine products, it is essential that the passaging methods used maintain the undifferentiated state and high proliferation potency of the cells. MEF cells or similar cells (such as STO cells) are usually used as feeder cells for ES/EG cells to maintain the undifferentiated state and high proliferation potency of the cells. Addition of fetal bovine serum (hereinafter, FBS) to the culture medium is also important, and it is crucial to select an FBS product which is suited for the culturing of the ES/EG cells, usually with the addition of FBS at about 10-20%. Also, LIF has been identified as a factor that maintains the undifferentiated state of ES/EG cells derived from mouse embryo (Smith & Hooper, Dev. Biol. 121:1, 1987; Smith et al., Nature 336:688, 1988; Rathjen et al., Genes Dev. 4:2308, 1990), and addition of LIF to culture can more effectively maintain the undifferentiated state (see the following literature: Manipulating the Mouse Embryo: *A Laboratory Manual* (Hogan et al., Cold Spring Harbor Laboratory Press, 1994 (Non-patent document 1) and Embryonic Stem Cells (Turksen ed., Humana Press, 2002) (Non-patent document 2)).

However, the culturing methods employed for these classical ES/EG cells are not suitable methods when human ES (or EG) cells are used for regenerative medicine or other practical purposes. One reason for this is that human ES cells are unresponsive to LIF, and lack of feeder cells causes death of the cells or loss of the undifferentiated state and differentiation into different cell types (Thomson et al., Science 282:1145, 1998). The use of feeder cells itself is another problem because such co-culturing systems increase production cost and are poorly suited for large-scale culturing, while separation and purification of the ES cells from the feeder cells is required when the ES cells are to be actually used. In the future, when human ES cells and other pluripotent stem cells are utilized as cell sources for regenerative medicine, and particularly for cell transplantation therapy, the use of non-human animal cell products such as MEF cells and FBS will not be desirable because of risks including potential infection of the ES cells by heterozoic viruses and contamination with antigenic molecules that may be recognized as heteroantigens (Martin et al., Nature Med. 11:228, 2005).

Consequently, in order to refine ES/EG cell culturing methods and modify them to be suitable for future implementation, active efforts are being made to develop FBS substitutes (International Patent Publication No. WO98/30679) and to utilize human cells as feeders instead of MEF cells (Richards et al., Nature Biotech. 20:933, 2002; Cheng et al., Stem Cells 21:131, 2003; Hovatta et al., Human Reprod. 18:1404, 2003; Amit et al., Biol. Reprod. 68:2150, 2003). Development of culturing methods using no feeders is another alluring prospect. Carpenter and coworkers have reported that seeding of ES cells in a Matrigel- or Laminin-coated culturing plate and addition of MEF cell conditioned medium to the culture medium allows prolonged culturing of human ES cells which retain their undifferentiated and pluripotency (Xu et al., Nature Biotech. 19:971, 2001 (Non-patent document 3); International Patent Publication No. WO01/51616 (Patent document 1)). The same group also succeeded in constructing a more effective ES cell culturing system by developing a serum-free medium containing added bFGF/FGF-2 or Stem Cell Factor (hereinafter, SCF)(International Patent Publication No. WO03/020920 (Patent document 2)). An ES cell culturing system using the same serum-free medium and requiring no feeder has also been reported by an Israeli research group (Amit et al., Biol. Reprod. 70:837, 2004 (Non-patent document 4)). Recently, a method of maintaining the undifferentiated state of human ES cells by addition of bFGF/FGF-2 and the bone morphogenetic protein antagonist Noggin has also been reported (Xu et al., Nature Methods 2:185, 2005). Separately, it has been shown that simple addition of Glycogen Synthase Kinase (GSK)-3 inhibitor to culture medium can efficiently maintain the undifferentiated state of murine and human ES cells without addition of growth factors or the like and without using feeder cells (Sato et al., Nature Med. 10:55, 2004 (Non-Patent document 5)).

Thus, while new methods are being proposed for culturing of pluripotent stem cells without the use of feeder cells, actual implementation and industrial use of such cells will require even greater convenience of pluripotent stem cell growth effects and culturing methods.

One well known factor that maintains the undifferentiated state of murine ES/EG cells and increases their proliferation potency is the LIF mentioned above, and while the LIF-related IL-6 family of molecules falls under this category (Yoshida et al., Mech. Dev. 45:163, 1994; Koshimizu et al., Development 122:1235, 1996), very few other examples have been reported. Recently, serum-free medium containing added bFGF/FGF-2 or SCF has been reported to notably promote the proliferation potency of human ES cells (International Patent Publication No. WO03/020920 (Patent document 2)).

Given the active, i.e., proliferating, nature of ES cells in comparison to other cell types, few attempts have been made to actually investigate their proliferation potency; however, the needs of regenerative medicine will require increased proliferation of such cells.

One of the problems currently encountered in culturing pluripotent stem cells is that the cells generally form tight colonies and are therefore difficult to handle for passaging and the like. Undifferentiated ES/EG cells are usually found in a condition with the cells firmly adhering to each other, forming colonies, i.e. cell masses with indistinct boundaries between cells. For provision of ES/EG cells for passaging or differentiation-inducing experiments, it is therefore necessary to disperse the colonies in as short a period as possible by treatment with protease solutions of trypsin or the like. When this is done, however, dispersion of the ES/EG cell colonies into individual cells requires relatively high-concentration protease treatment and/or vigorous mechanical stirring, and such procedures significantly reduce the viability and adhesion ability of the ES/EG cells.

Moreover, since ES/EG cells undergo spontaneous differentiation during continuous culturing in a clustered condition, they must be dispersed to single cells during passaging and the passaging must be carried out before colonies grow to an excessive size. Murine ES cells, for example, generally require each passaging to be conducted for 2-3 days, and if the passaging is not conducted by a suitable method, cells that have deviated from their undifferentiated state may appear in the cluster, rendering the cells unsuitable for use. This cannot be overcome simply by adding a sufficient amount of a factor that maintains the undifferentiated state of ES/EG cells, such as the LIF mentioned above or GSK-3 inhibitors, and excessive colony growth and cells with a differentiated phenotype are induced. Therefore, a method of growing ES/EG cells without formation of colonies, i.e., with the cells individually dispersed, is expected to be highly useful for providing ES/EG cells for industrial use. However, no such attempts or successes can be found to date.

The present inventors have previously seeded F9 cells, an embryonal carcinoma cell line known to normally proliferate by colony formation, on a culture plate coated with E-cadherin (Nagaoka et al., Biotechnol. Lett. 24:1857, 2002 (Non-patent document 6)) and have found that this prevents formation of cell colonies (International Symposium on Biomaterials and Drug Delivery Systems, 2002 Apr. 14-16, Taipei, Taiwan; 1st Meeting of the Japanese Society for Regenerative Medicine, 2002 Apr. 18-19, Kyoto, Japan). Specifically, F9 cells exhibited a dispersed cell morphology on a culturing plate having E-cadherin, which is a known cell adhesion molecule for F9 cells, immobilized on an untreated polystyrene culturing plate (hereinafter, "E-cad plate").

F9 cells exhibit a phenotype somewhat similar to ES cells, expressing alkaline phosphatase (hereinafter, ALP) or SSEA-1 and Oct-3/4, which are known as specific ES/EG cell markers (Lehtonen et al., Int. J. Dev. Biol. 33:105, 1989, Alonso et al., Int. J. Dev. Biol. 35:389, 1991). However, F9 cells do not require feeder cells or LIF for maintenance of the undifferentiated state of the cells, and therefore are different in their mechanism of maintaining undifferentiation. Moreover, whereas ES cells have triploblast differentiating potential to all three germ layers, the differentiation of F9 cells is limited to endodermal cells, and they are unable to form chimeras. In other words, although F9 cells are used as an ES/EG cell model system in some experiments, they differ from ES/EG cells in many aspects involving the culturing method and culturing conditions.

Thus, it was not possible to predict, based on the scientific evidence, whether the aforementioned E-cad plate can be used in ES cell culturing methods that require no feeder cells, whether ES cells cultured by such methods can be passaged while maintaining their undifferentiated state and pluripotency, and whether the proliferation potency of the ES cells can be increased. In fact, the proliferation potency of F9 cells cultured on an E-cad plate is roughly equivalent to that of F9 cells cultured on a conventional cell culturing plate, and no data had been obtained to suggest that the proliferation potency of ES cells could thereby be increased.

E-cadherin is known to be expressed by undifferentiated murine ES cells, and it is also known that intercellular adhesion is notably inhibited with ES cells that lack E-cadherin gene expression due to gene modification (Larue et al., Development 122:3185, 1996). However, it has not yet been attempted to use E-cadherin as an adhesion substrate in an ES/EG cell culturing method.

In addition to the efficient culturing methods described above, when pluripotent stem cells such as ES cells are to be used as a laboratory material or for production of regenerative medicine products, it is also necessary to design methods for efficiently introducing selected exogenous genes into the cells and expressing them. In particular, one strategy for applying ES cells in regenerative medicine for treatment of various diseases is to modify the cell properties, such as proliferation and differentiation potency or the drug sensitivity, and this can be satisfactorily realized by introducing and expressing appropriate exogenous genes in the cells. In the case of murine ES cells, it is widely known that genes can be artificially modified to produce transgenic mice or knockout mice, for which efficient gene transfer methods are especially useful.

Ordinary transfer of exogenous genes into cells is frequently accomplished using agents such as calcium phosphate, DEAE-dextran and cationic lipid preparations. However, application of such methods to ES cells is known to result in lower efficiency than for other cell types (Lakshmipathy et al., Stem Cells 22:531, 2004 (Non-patent document 8)). Methods using various viral vectors for transfer of exogenous genes have also been reported. For example, retroviral vectors (Chemy et al., Mol. Cell. Biol., 20:7419, 2000), adenovirus vectors (Smith-Arica et al., Cloning Stem Cells 5:51, 2003), lentivirus vectors (Amaguchi et al. J. Virol. 74:10778, 2000; Asano et al., Mol. Ther. 6:162, 2002; International Patent Publication No. WO02/101057), and Sendai virus vectors (Sasaki et al., Gene Ther. 12:203, 2005; Japanese Unexamined Patent Publication No. 2004-344001) are publicly known. Nevertheless, the construction and preparation of viral vectors require relatively complex and time consuming, while biological safety is also an issue, depending on the virus, and therefore such methods are neither convenient nor universally employed.

Consequently, exogenous gene transfer into ES cells is most commonly carried out by a method known as electroporation. This technique involves application of an electrical pulse to cells to transiently open pores in the cell membranes for introduction of an exogenous gene into the cells, and it is a highly flexible method. Recently, an improved technique called nucleofection has been established, whereby an exogenous gene is transferred directly into cell nuclei to achieve significantly higher expression efficiency (Lorenz et al., Biotech. Lett. 26:1589, 2004; Lakshmipathy et al., Stem Cells 22:531, 2004 (Non-patent document 8)). However, this method requires a special electrical pulse-generating device, and it is not easy to prepare the optimal conditions. Furthermore, it is necessary to first treat the cells with a protease such as trypsin to disperse the individual cells, and therefore the cell toxicity is relatively high.

Thus, the most useful gene transfer methods for pluripotent stem cells such as ES cells would be methods using gene transfer agents that are inexpensive and convenient to prepare, and would allow efficient transfer of exogenous genes into cells being cultured in an incubator.

Non-patent document 1: Manipulating the Mouse Embryo: *A Laboratory Manual* (Hogan et al., Cold Spring Harbor Laboratory Press, 1994).

Non-patent document 2: Embryonic Stem Cells (Turksen, ed. Humana Press, 2002).

Non-patent document 3: Xu et al., Nature Biotech. 19:971, 2001.

Non-patent document 4: Amit et al., Biol. Reprod. 70:837, 2004.

Non-patent document 5: Sato et al., Nature Med. 10:55, 2004.

Non-patent document 6: Nagaoka et al., Biotechnol. Lett. 24:1857, 2002.

Non-patent document 7: Nagaoka et al., Protein Eng. 16:243, 2003.

Non-patent document 8: Lakshmipathy et al., Stem Cells 22:531, 2004.

Patent document 1: International Patent Publication No. WO01/51616.

Patent document 2: International Patent Publication No. WO03/020920.

SUMMARY OF THE INVENTION

In light of these circumstances, it is an object of the present invention to provide a method for culturing pluripotent stem cells such as ES cells without using feeder cells, wherein the proliferation potency of the cells is augmented and the gene transfer efficiency is increased.

In order to solve the problems described above, the present inventors studied the possibilities of increasing proliferation potency and increasing gene transfer efficiency for ES cells, by culturing the cells in a state without colony formation, or in other words, in a dispersed state.

As mentioned above, the present inventors have succeeded in culturing F9 cells, an embryonal carcinoma cell line, without colony formation, i.e., in a dispersed state. When a cell culturing plate which had E-cadherin immobilized or coated on a solid phase surface (E-cad plate) was prepared and F9 cells were seeded on the plate, the F9 cells exhibited a dispersed cell morphology without colony formation. The proliferation potency was essentially the same for F9 cells cultured on the E-cad plate and F9 cells cultured on an ordinary plate.

When it was attempted to seed ES cells on an E-cad plate, virtually all of the cells adhered to the plate, and they exhibited a dispersed cell morphology without colony formation, similar to F9 cells. Most notably, the proliferation potency of ES cells seeded on the E-cad plate under these culturing conditions was significantly higher than the proliferation potency of ES cells cultured on an ordinary plate. Also, the exogenous gene transfer efficiency and expression level were significantly higher as well.

It was further confirmed that ES cells passaged multiple times on an E-cad plate are still undifferentiated and maintain their pluripotency if a factor that maintains undifferentiation is added to the liquid medium. In addition, it was demonstrated that ES cells prepared by the aforementioned method can be induced to differentiate into functional differentiated cells such as neurons and cardiomyocytes by using known methods, and that chimeric mice can be generated by transplanting them into mouse early embryos, and the present invention was thereby completed.

Therefore, according to a first mode of the invention there is provided a novel method of growing pluripotent stem cells, such as ES cells, which requires no feeder cells. The method of the invention is characterized in that the culturing vessel used has a pluripotent stem cell-adhering molecule immobilized or coated on a substrate solid phase surface at a predetermined density, whereby the cells can be cultured in a dispersed state for increased proliferation ability. The pluripotent stem cells prepared in this manner retain their undifferentiated state and pluripotency.

According to a second mode, the method of the invention is characterized in that the culturing vessel used has a pluripotent stem cell-adhering molecule immobilized or coated on a substrate solid phase surface at a predetermined density, whereby culturing of the cells in a dispersed state can increase the gene transfer efficiency into the cells.

As another working mode, the invention relates to pluripotent stem cells having an undifferentiated state and pluripotency, which are prepared by the method disclosed by the invention. For the purposes of the present disclosure, the "undifferentiated" state of pluripotent stem cells can be confirmed by expression of at least one undifferentiation marker.

According to another working mode, the invention relates to differentiated cells produced, by appropriate differentiation inducing treatment, from pluripotent stem cells prepared by the method disclosed for the invention. The differentiated cells are not particularly restricted as long as they are of a cell type whose differentiation can generally be induced from pluripotent stem cells. Specifically, there may be mentioned ectodermal cells or ectoderm-derived cells, mesodermal cells or mesoderm-derived cells, endodermal cells or endoderm-derived cells, and the like.

According to another working mode, the invention relates to a method of generating a chimeric embryo or chimeric animal using pluripotent stem cells prepared by the method disclosed for the invention, and to the generated chimeric embryo or chimeric animal.

The present invention primarily relates to the following aspects.

(1) A growing method for pluripotent stem cells, characterized by growing the pluripotent stem cells in a dispersed state while maintaining their undifferentiated state and pluripotency, using a liquid medium and a culturing vessel having immobilized or coated on a substrate solid phase surface a molecule which is adhesive to the pluripotent stem cells, without using feeder cells.

(2) A gene transfer method for pluripotent stem cells, characterized by efficiently transferring a gene into the pluripotent stem cells and expressing it, using a liquid medium and a culturing vessel having immobilized or coated on a substrate solid phase surface a molecule which is adhesive to the pluripotent stem cells.

(3) The method of (1) or (2) above, wherein the molecule which is adhesive to the pluripotent stem cells is either a molecule that is expressed by the pluripotent stem cells, or a molecule that is structurally homologous with the molecule and has homophilic binding ability with the pluripotent stem cells.

(4) The method of (3) above, wherein the molecule which is adhesive to the pluripotent stem cells is a molecule belonging to the cadherin family.

(5) The method of (4) above, wherein the molecule belonging to the cadherin family is E-cadherin, or a molecule which has structural homology with that molecule, which comprises the EC1 domain and one or more domains from among the EC2 domain, EC3 domain, EC4 domain and EC5 domain of E-cadherin, and which has homophilic binding ability with the pluripotent stem cells.

(6) The method of (5) above, wherein the E-cadherin is derived from a mammal.

(7) The method of (6) above, wherein the E-cadherin is derived from a human or mouse.

(8) The method of any one of (1) to (7) above, wherein the molecule which is adhesive to the pluripotent stem cells is fused with an immunoglobulin Fc region and is immobilized on the substrate solid phase surface via the Fc region.

(9) The method of any one of (1) to (8) above, wherein the pluripotent stem cells are mammalian embryonic stem cells (ES cells) or embryonic germ cells (EG cells).

(10) Pluripotent stem cells produced by the method of any one of (1) to (9) above.

BRIEF DESCRIPTION OF THE DRAWINGS

FIG. 4A is a set of photographs showing expression of a marker for an undifferentiated state of ES cells seeded on an E-cad-Fc plate. The ES cells (EB3 cell line) were seeded on a gelatin plate (indicated as Cont) or an E-cad-Fc plate, and ALP activity was detected on the 14th day of culturing. In this figure, LIF(+) and (−) respectively indicate addition/non-addition of LIF to the culturing medium.

FIG. 4B is a set of photographs showing expression of markers for undifferentiated ES cells seeded on an E-cad-Fc plate. The ES cells (EB3 cell line) were seeded on a gelatin plate (indicated as Cont) or an E-cad-Fc plate, and Oct-3/4 protein was detected on the 14th day of culturing. DAPI: Nuclear staining with DAPI. Merged: Superposition of DAPI and Oct-3/4 antibody stain.

FIG. 8 is a pair of photographs showing pluripotency of ES cells passaged on an E-cad-Fc plate. ES cells (R1 line) seeded on the E-cad-Fc plate were induced to differentiate into neurons (upper) and cardiomyocytes (lower). These photos show images of the cells fixed on the 12th day after inducing differentiation and stained with antibody for markers specific to neurons and cardiomyocytes.

DETAILED DESCRIPTION OF THE INVENTION

Definitions

Figure 1:
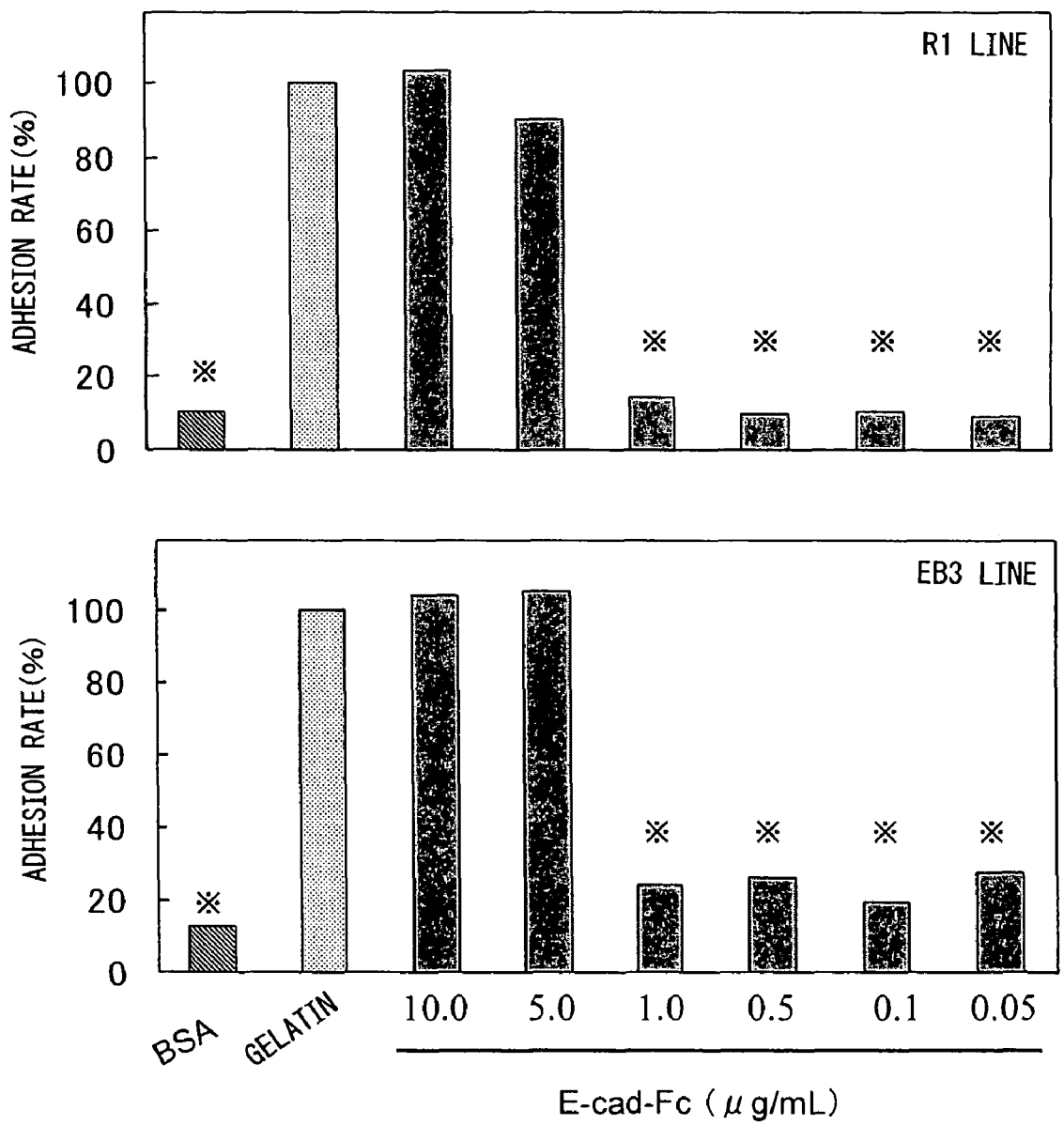
FIG. 1 is a pair of graphs showing adhesion of ES cells (R1 and EB3 cell lines) to E-cad-Fc coated on a polystyrene plate. The adhesion rate represents a relative value in which 100% is the number of ES cells adhering to a plate coated with gelatin (0.1%). BSA: Group with ES cells adhered to plate coated with 0.1% bovine serum albumin. *: with respect to gelatin group, $p<0.01$.

The term "pluripotent stem cells" as used throughout the present specification refers to cells capable of prolonged or virtually indefinite proliferation in vitro while retaining their undifferentiated state, exhibiting normal karyotype (chromosomes) and having the capacity to differentiate into all three germ layers (ectoderm, mesoderm and endoderm) under the appropriate conditions. The term "pluripotent stem cells" includes, but is not limited to, ES cells isolated from early embryo and their analogous EG cells isolated from fetal-stage primordial germ cells. Throughout the present specification, "ES cells" will be used to include "EG cells".

The term "undifferentiated state" as used throughout the present specification means the nature of pluripotent stem cells exhibiting a state of undifferentiation that can be confirmed based on one or more undifferentiated ES cell markers such as ALP activity or Oct-3/4 gene (product) expression, or based on expression of various antigenic molecules. The state of undifferentiation of pluripotent stem cells means that the pluripotent stem cells are capable of prolonged or virtually indefinite proliferation and exhibit normal karyotype (chromosomes), while having the capacity to differentiate into all three germ layers under the appropriate conditions.

The term "pluripotency" as used throughout the present specification refers to the ability to differentiate into a variety of cell types. The differentiated cells are not particularly restricted as long as they are of a cell type in which differentiation can generally be induced from pluripotent stem cells. Specifically, there may be mentioned ectodermal cells or ectoderm-derived cells, mesodermal cells or mesoderm-derived cells, endodermal cells or endoderm-derived cells, and the like.

The term "liquid medium" as used throughout the present specification includes any liquid medium that can be used for conventional methods of passaging pluripotent stem cells.

The term "pluripotent stem cell-adhering molecule" as used throughout the present specification may refer to a molecule that binds and adheres with affinity to pluripotent stem cells, and it may be any of various types such as a protein, peptide, saccharide chain, low molecular compound (drug) or the like. As pluripotent stem cell-adhering molecules, there are preferred molecules that are expressed in the cells and have homophilic binding ability, and as examples there may be mentioned the cadherin family of molecules. E-cadherin is known to be expressed by undifferentiated ES cells and is therefore preferred for use, but there is no particular restriction thereto. When the adhering molecule is a protein or peptide molecule, a peptide fragment thereof may be used as long as it has the same adhering activity as the protein or peptide molecule.

A pluripotent stem cell-adhering molecule can be used for the culturing method of the invention by being immobilized or coated onto the solid phase surface of a culturing vessel or culture substrate (hereinafter also collectively referred to "culture substrate"). As culture substrates for the invention there may be used any ones that are conventionally used for cell culturing, such as a plate or flask. These culture substrates may be made of inorganic materials such as glass, or of organic materials such as polystyrene or polypropylene, but they are preferably sterilizable materials with high heat resistance and moisture resistance.

The method applied for immobilizing or coating the pluripotent stem cell-adhering molecule onto the solid phase surface of the culture substrate may be a physical method such as adsorption or a chemical method such as covalent bonding, but an adsorption method is preferred for ease of operation. Also, an artificial antigenic molecule may be added to or fused with the adhering molecule beforehand in order to utilize binding of specific antibodies for the antigenic molecule. In this case, the specific antibodies must be immobilized or coated on the solid phase surface of the culture substrate beforehand by a physical method such as adsorption or a chemical method such as covalent bonding.

The culture substrate prepared in this manner can be used directly for ordinary culturing of the pluripotent stem cells. That is, an appropriate number of pluripotent stem cells may be suspended in a commonly employed liquid medium or cell culture medium, and the mixture applied to the culture substrate. Subsequent liquid medium replacement and passaging may also be carried out in the same manner as in conventional methods.

The term "homophilic binding" as used throughout the present specification refers to cell-cell or cell-substrate binding via adhesion molecules that involves binding or association between the same type of adhesion molecule.

The term "feeder cells" as used throughout the present specification refers to separate cells, also known as support cells, that are cultured beforehand and perform the role of supplying nutrients and growth factors which are missing in the medium used for culturing cells which would be unable to survive and grow on their own. "Feeder cells" include, but are not limited to, MEF cells and stromal cells such as STO cells.

The term "dispersed state" as used throughout the present specification refers to a state of growing cells adhered to a culture substrate surface, wherein no distinct colonies are formed and the individual cells are either not in contact with other cells or if partially in contact, have a very small area of contact.

The term "gene" as used throughout the present specification means genetic material, and refers to nucleic acid including transcription units. A gene may be of RNA or DNA, and may be a naturally occurring or artificially designed sequence. Also, the gene need not code for a protein necessarily, and for example, it may code for functional RNA such as a ribozyme or siRNA (short/small interfering RNA).

Other advantages and features of the invention in addition to the effect described above will be explained in the detailed description of the preferred embodiments provided hereunder.

Unless otherwise specified, gene engineering methods employed in molecular biology and recombinant DNA technology, as well as common cell biology protocols and conventional techniques, may be employed for carrying out the invention, with reference to standard literature in the field. These include, for example, Molecular Cloning: *A Laboratory Manual*, 3rd Edition (Sambrook & Russell, Cold Spring Harbor Laboratory Press, 2001); Current Protocols in Molecular Biology (Ausubel et al. ed., John Wiley & Sons, 1987); Methods in Enzymology Series (Academic Press); PCR Protocols: Methods in Molecular Biology (Bartlett & Stirling, eds., Humana Press, 2003); Animal Cell Culture: A Practical Approach, 3rd Edition (Masters ed., Oxford University Press, 2000); and Antibodies: *A Laboratory Manual* (Harlow et al. & Lane ed., Cold Spring Harbor Laboratory Press, 1987). The reagents and kits used for the cell culturing and cell biology experiments referred to throughout the present specification are available from commercial vendors such as Sigma, Aldrich, Invitrogen/GIBCO, Clontech and Stratagene.

Also, ordinary methods for cell culturing and development and cell biology experiments using the pluripotent stem cells may be carried out with reference to standard literature in the field. These include Guide to Techniques in Mouse Development (Wasserman et al. ed., Academic Press, 1993); Embryonic Stem Cell Differentiation in vitro (M. V. Wiles, Meth. Enzymol. 225:900, 1993); Manipulating the Mouse Embryo: *A Laboratory Manual* (Hogan et al. ed., Cold Spring Harbor Laboratory Press, 1994); and Embryonic Stem Cells (Turksen ed., Humana Press, 2002). The reagents and kits used for the cell culturing and development and cell biology experiments referred to throughout the present specification are available from commercial vendors such as Invitrogen/GIBCO and Sigma.

Standard protocols have already been established for generation, passaging and preservation of murine and human pluripotent stem cells, and these may be carried out using the pluripotent stem cells with reference to the literature mentioned above, as well as an abundance of other literature (Matsui et al., Cell 70:841, 1992; Thomson et al., U.S. Pat. No. 5,843,780; Thomson et al., Science 282:114, 1998; Shamblott et al., Proc. Natl. Acad. Sci. USA 95:13726, 1998; Shamblott et al., U.S. Pat. No. 6,090,622; Reubinoff et al., Nat. Biotech. 18:399, 2000; International Patent Publication No. WO00/27995). Methods are also known for establishing ES cells or ES-like cell lines for other animal species such as, for example, monkeys (Thomson et al., U.S. Pat. No. 5,843, 780; Proc. Natl. Acad. Sci. USA, 92, 7844, 1996), rats (Iannaccone et al., Dev. Biol. 163:288, 1994; Loring et al., International Patent Publication No. WO99/27076), chickens (Pain et al., Development 122:2339, 1996; U.S. Pat. No. 5,340,740; U.S. Pat. No. 5,656,479), pigs (Wheeler et al., Reprod. Fertil. Dev. 6:563, 1994; Shim et al., Biol. Reprod. 57:1089, 1997) and the like, and the ES cells used for the invention may be prepared according to methods described for each.

ES cells are pluripotent stem cells isolated as an aggregate of undifferentiated stem cells by extracting the cell mass in the interior of the blastocyst-stage embryo, known as an inner cell mass, and transferring it to in vitro culture, with repeated detachment and passaging of the cell mass. As murine ES cells, there are known various lines including E14, D3, CCE, R1, J1, EB3 and the like, some of which may be obtained from the American Type Culture Collection, Cell & Molecular Technologies or Thromb-X. Currently, 50 human ES cell lines have been established throughout the world, and 20 different lines are registered at the U.S. National Institutes of Health (NIH) (http://stemcells.nih.gov/registry/index.asp). Some of these may be obtained from ES Cell International or the Wisconsin Alumni Research Foundation.

ES cell lines are usually established by culturing of early embryos, but ES cells can also be produced from early embryos obtained by nuclear transfer of somatic cell nuclei (Munsie et al., Curr. Biol. 10:989, 2000; Wakayama et al., Science 292:740, 2001; Hwang et al., Science 303: 1669, 2004). There have also been proposed methods for generating ES cells from blastocyst-stage embryo-like cellular structures obtained by transferring cell nuclei of desired animals into another species of oocytes or denucleated oocytes divided into several portions (known as cytoplasts or ooplastoids) (International Patent Publication Nos. WO99/45100; WO01/46401; WO01/96532; U.S. Pregnant Publication Nos. 02/90722; 02/194637). There have also been reported, for example, an attempt to produce ES cells from a parthenogenetic embryo developed to the same stage as the blastocyst-stage (U.S. Pregnant Publication No. 02/168763; Vrana K et al., Proc. Natl. Acad. Sci. USA 100:11911-6), and a method of fusing ES cells with somatic cells to produce ES cells having the genetic information of the somatic cell nuclei (International Patent Publication No. WO00/49137; Tada et al., Curr. Biol. 11:1553, 2001). The ES cells used for the invention include ES cells produced by such methods and ES cells whose chromosomal DNA has been modified by genetic engineering techniques.

EG cells used for the invention are produced by stimulating fetal germ cells known as primordial germ cells on feeder cells such as MEF cells, STO cells or Sl/Sl$^4$-m220 cells with a chemical agent such as LIF, bFGF/FGF-2 or forskolin in the same manner as ES cells (Matsui et al., Cell 70:841, 1992; Koshimizu et al., Development 122:1235, 1996), and their properties are very similar to those of ES cells (Thomson & Odorico, Trends Biotechnol. 18:53, 2000). As with ES cells, EG cells produced by fusing EG cells with somatic cells (Tada et al., EMBO J. 16:6510, 1997; Andrew et al.) and EG cells whose chromosomal DNA has been modified by genetic engineering techniques, may also be used for the method of the invention.

Moreover, pluripotent stem cells to be used for the growing method of the invention are not limited to ES cells or EG cells, but include all pluripotent stem cells derived from a mammalian embryo or fetus, umbilical cord, or adult tissue or blood, such as adult organs or bone marrow, and having ES/EG cell-like features. For example, ES-like cells obtained by culturing germ cells under special culturing conditions exhibit features extremely similar to ES/EG cells (Kanatsu-Shinohara et al., Cell 119:1001, 2004), and may be used as pluripotent stem cells. As another example there may be mentioned multipotent adult progenitor/stem cells (MAPC) isolated from bone marrow cells and having the potential to differentiate into all three germ layers. Moreover, pluripotent stem cells obtained by culturing root sheath cells or keratinocytes (International Patent Publication No. WO02/51980), intestinal epithelial cells (International Patent Publication No. WO02/57430) or inner ear cells (Li et al., Nature Med. 9:1293, 2003) under special culturing conditions, and pluripotent stem cells produced by treatment of blood mononuclear cells (or stem cells contained in their cell fraction) with M-CSF (Macrophage-Colony Stimulating Factor)+PMA (phorbol 12-myristate 13-acetate)(Zhao et al., Proc. Natl. Acad. Sci. USA 100:2426, 2003) or CR3/43 antibody (Abuljadayel, Curr. Med. Res. Opinion 19:355, 2003), are also all included as long as their features resemble those of ES/EG cells. In this case, features resembling ES/EG cells may be defined as cell biology properties unique to ES/EG cells, such as the presence of surface (antigenic) markers specific to the cells and expression of genes specific to the cells, as well as teratoma-forming potential and chimeric mouse-forming potential.

The present invention relates to a method of culturing pluripotent stem cells including ES cells and is characterized by using molecules that adhere to pluripotent stem cells (hereinafter referred to as "pluripotent stem cell-adhering molecules"). The pluripotent stem cell-adhering molecules used for carrying out the invention are used for the culturing method of the invention by being immobilized or coated on the solid phase surface of a culturing vessel or culture substrate (hereinafter also collectively referred to culture substrate). Any culture substrate may be used as the culture substrate of the invention as long as it allows culturing of pluripotent stem cells, but preferably it is one used in the prior art for cell culturing. As examples of culture substrates for cell culturing there may be mentioned a dish, plate, flask, chamber slide, tube, cell factory, roller bottle, spinner flask, hollow fibers, microcarriers, beads and the like. These culture substrates may be made of inorganic materials such as glass, or of organic materials such as polystyrene, but it is preferable to use materials such as polystyrene that have high adsorption properties for proteins and peptides, or materials that have been treated by, for example, hydrophilic treatment or hydrophobic treatment for increased adsorption properties. Also preferred are sterilizable materials with high heat resistance and moisture resistance. As an example of such a preferred substrate there may be mentioned a polystyrene dish and/or plate with no special cell culturing treatment (hereinafter referred to as "untreated polystyrene plate"), most commonly used for culturing of E. coli and the like, and such culture substrates are commercially available.

A pluripotent stem cell-adhering molecule is a molecule that binds and adheres with affinity to pluripotent stem cells, and it may be any of various types such as a protein, peptide, saccharide chain, low molecular compound, or a molecule composed of two or more of these. Few adhesion molecules have been reported for undifferentiated ES/EG cells, but they are known to express, for example, ICAM-1, VCAM-1 and NCAM belonging to the immunoglobulin superfamily (Tian et al., Biol. Reprod. 57:561, 1997). The pluripotent stem cell adhesion molecule is preferably one that is expressed on the cell membrane surfaces of the pluripotent stem cells used, and more preferably it is a molecule with homophilic binding ability. Homophilic binding for cell adhesion means cell-cell or cell-substrate binding via adhesion molecules that involves binding or association between the same type of adhesion molecule. Known adhesion molecules having such properties include NCAM, L1, plexin and cadherin, among which members of the cadherin family of molecules are preferably used from the standpoint of adhesion strength. It has been reported that E-cadherin is specifically expressed by undifferentiated ES cells (Larue et al., Development 122:3185, 1996), and therefore this molecule is preferred for use. However, the adhesion molecules to be used are not limited to E-cadherin, and any of the cadherin family of molecules or homophilic binding adhesion molecules expressed by pluripotent stem cells may be used. Also, gene modification of ES cells by a genetic engineering technique resulting in expression of a full-length or partial gene coding for a molecule with homophilic binding ability, even if it is not normally expressed by ES cells, may be carried out for use of the molecule in the method of the invention.

Cadherins are adhesion molecules involved in $Ca^{2+}$-dependent intercellular adhesion and binding known as adhesive binding or adherens junction binding, and the three types, E (epithelial)-cadherin, N (neural)-cadherin and P (placental)-cadherin are well-known. These cadherin molecules are membrane-bound glycoproteins composed of 700-750 amino acid residues, and the extracellular region comprises five repeating structures, known as extracellular cadherin (EC) domains, consisting of about 110 amino acid residues. For example, the domains of human E-cadherin (amino acid sequence listed as SEQ ID NO: 1) are EC1, EC2, EC3, EC4 and EC5, respectively corresponding to amino acid residues 157-262, 265-375, 378-486, 487-595 and 596-700 (where the numbers are those of the residues of the amino acid sequence listed as SEQ ID NO: 1). Also, the domains of murine E-cadherin (amino acid sequence listed as SEQ ID NO: 2) are EC1, EC2, EC3, EC4 and EC5, respectively corresponding to amino acid residues 159-264, 267-377, 380-488, 489-597 and 598-702 (where the numbers are those of the residues of the amino acid sequence listed as SEQ ID NO: 2). These EC domains are homologous among different cadherin molecules, with particularly high homology between the domains situated near the N-terminal (EC1, EC2). Currently, more than 50 cadherin molecules are known to exhibit such similar structure, and these have been grouped together as the cadherin family. Reviews on cadherins may be found in Takeichi, Curr. Opin. Cell Biol. 7: 619, 1995; Marrs & Nelson, Int. Rev. Cytol. 165:159, 1996; Yap et al., Annu. Rev. Cell Dev. Biol. 13:119, 1997; Yagi & Takeichi, Genes Dev. 14:1169, 2000; Gumbiner, J. Cell Biol. 148:399, 2000; and elsewhere.

E-cadherin (also, cadherin-1) is widely expressed in epithelial cells such as parenchymal cells of internal organs such as the liver, kidneys and lungs, and in keratinocytes, and it is known to be an important adhesion molecule for intercellular adhesion (see reviews in Mareel et al., Int. J. Dev. Biol. 37:227, 1993; Mays et al., Cold Spring Harb. Symp. Quant. Biol. 60:763, 1995; El-Bahrawy & Pignatelli, Microsc. Res. Tech. 43:224, 1998; Nollet et al., Mol. Cell. Biol. Res. Commun. 2:77, 1999). Also, E-cadherin is abundantly expressed on undifferentiated murine ES cells, and it is known that ES cells lacking E-cadherin expression due to genetic engineering have notably inhibited intercellular adhesion (Larue et al., Development 122:3185, 1996). Moreover, it can be confirmed that E-cadherin genes are also expressed in human ES cell lines, based on data stored at the public gene expression database at the U.S. National Center for Biotechnology Information (NCBI).

The method of producing cadherin molecules such as E-cadherin or other adhesion molecules for carrying out the invention, if the molecule is a protein or peptide, preferably involves production, purification and use of a recombinant protein using molecular biological techniques, although this is not restrictive. Other methods with comparable results may be employed, and for example, a pluripotent stem cell adhesion molecule may be used after extraction and purification from living tissue or cells, or a peptide may be chemically synthesized for use.

Standard protocols have already been established for methods of producing recombinant proteins and obtaining genes coding for such proteins, as pluripotent stem cell adhesion molecules, and reference may be made to the literature cited above, although there is no restriction thereto. Taking E-cadherin as an example, the E-cadherin gene has already been isolated and identified for animals including human (SEQ ID NO: 1), mouse (SEQ ID NO: 2) and rat, and the respective nucleotide sequences are accessible from public DNA databases such as NCBI (Accession Nos.: (human) NM_004360; (mouse) NM_009864; (rat) NM_031334). A person skilled in the art can therefore design a primer or probe specific for the E-cadherin gene of interest and use it in ordinary molecular biological techniques to obtain and use cDNA for the E-cadherin gene. Alternatively, cDNA for the E-cadherin gene may be obtained from the RIKEN Gene Bank (Tsukuba, Japan) or the American Type Culture Collection (ATCC), or Invitrogen/ResGen. The gene coding for the adhesion molecule used is preferably derived from the same animal species from which the pluripotent stem cells are derived, and for example, when the invention is carried out using murine ES cells it is preferred to use cDNA of murine E-cadherin. However, E-cadherin cDNA from different species, such as human, monkey, cow, horse, pig, sheep, bird (for example, chicken) or amphibian (for example, *Xenopus laevis*) may be used.

An example of a suitable method for producing a recombinant protein of an adhesion molecule to be used for carrying out the invention is characterized by transferring a gene coding for the molecule into mammalian cells such as COS cells, 293 cells or CHO cells and expressing it. Preferably, the gene is linked with a nucleic acid sequence allowing transcription and expression of the gene in a wide range of mammalian cells, i.e., a promoter sequence, in a manner so that transcription and expression are under the control of the promoter. The transcribed and expressed gene is also preferably linked to a polyA addition signal. As preferred promoters there may be mentioned promoters from viruses such as SV (Simian Virus) 40 virus, cytomegalovirus (CMV) or Rous sarcoma virus, or β-actin promoter, EF (Elongation Factor) 1α promoter or the like.

The gene used to produce the recombinant protein does not necessarily have to contain the full-length region of the gene coding for the molecule, as it may be a partial gene sequence as long as the protein or peptide molecule encoded by the partial sequence has adhesion activity equivalent to or exceeding that of the original molecule. For example, an E-cadherin suitable for use according to the invention may be a recombinant protein constructed from partial sequences including 690-710 amino acid residues from the N-terminal coding for the extracellular region, i.e., a protein comprising the EC1-EC5 domains. Because the domain nearest the N-terminal (EC1) of a cadherin molecule generally determines the binding specificity, or homophilic binding property, of the molecule (Nose et al., Cell 61:147, 1990), a protein molecule containing at least EC1 and lacking one or more of the other domains may be constructed and used. There may also be used a protein having at least 80%, preferably at least 85%, more preferably at least 90%, and most preferably at least 95% amino acid level homology with the aforementioned protein molecule, and exhibiting adhesion activity.

The recombinant protein mentioned above may also be produced as a fusion protein with another protein or peptide. For example, it may be produced as a fusion protein with an immunoglobulin Fc region or with GST (Glutathione-S-Transferase) protein, MBP (Mannose-Binding Protein), avidin protein, His (oligo histidine) tag, HA (HemAgglutinin), Myc tag, VSV-G (Vesicular Stomatitis Virus Glycoprotein) tag or the like, and a Protein A/G column or a specific antibody column may be used for convenient and efficient purification of the recombinant protein. An Fc-fusion protein is particularly preferred for carrying out the invention because it has a greater ability to adsorb onto culture substrates made of materials such as polystyrene.

Numerous genes coding for immunoglobulin Fc regions have already been isolated and identified in mammals, including humans. Many of their nucleotide sequences have been reported, and for example, sequence data for nucleotide sequences containing human IgG1, IgG2, IgG3 and IgG4 Fc regions are accessible from public DNA databases such as NCBI, those sequences being registered respectively as Accession Nos.: AJ294730, AJ294731, AJ294732 and AJ294733. Thus, a person skilled in the art can design a primer or probe specific for the Fc region and use it in ordinary molecular biological techniques to obtain and use cDNA coding for the Fc region. In this case, the animal species and subtype of the gene coding for the Fc region of interest is not particularly limited, but preferably the gene codes for the Fc region of human IgG1 or IgG2 or murine IgG2a or IgG2b, which have strong binding affinity for Protein A/G. Methods for enhancing binding affinity for Protein A by introducing mutations into Fc regions are known (Nagaoka et al., Protein Eng. 16:243, 2003 (Non-patent document 7)), and Fc proteins with genetic modifications by such methods may also be used.

Examples of methods for producing recombinant proteins for E-cadherin, which is preferred for carrying out the invention have been published in the literature by the present inventors (Nagaoka et al., Biotechnol. Lett. 24:1857, 2002 (Non-patent document 6); Protein Eng. 16:243, 2003 (Non-patent document 7)).

Also, there is commercially available is a purified recombinant protein produced by introducing into murine cells a fused gene obtained by linking cDNA having a sequence coding for the Fc region of human IgG and an His tag sequence to cDNA coding for the extracellular region of murine or human E-cadherin, and expressing the recombinant protein (Recombinant Human/Mouse E-cadherin-Fc Chimera; R&D systems, Genzyme Techne), which may be used as a mouse or human E-cadherin protein.

The method for immobilizing or coating the pluripotent stem cell adhesion molecule onto the solid phase surface of a culture substrate for carrying out the method disclosed by the invention may be a physical method such as adsorption or a chemical method such as covalent bonding, but an adsorption method is preferred for ease of execution. When the adhesion molecule is a protein or peptide molecule, or when it is a high molecular compound containing saccharide chains, the molecule can be easily adsorbed by contacting a solution of the molecule with the solid phase surface of a culture substrate such as a plate and removing the solvent after a prescribed period of time. More specifically, an adhesion molecule solution prepared using a solvent such as distilled water or PBS may be filtered and sterilized and then contacted with a culture substrate such as a plate, and it is allowed to stand for from a few hours to a full day/night period to obtain a cell culture substrate with the adhesion molecule immobilized or coated thereon. This is preferably used after rinsing several times with distilled water or PBS and replacing with a balanced saline solution such as PBS.

An artificial antigenic molecule is preferably added to or fused with the adhesion molecule beforehand because this will allow utilization of binding with antibodies specific for the antigenic molecule, and efficient attachment of the adhesion molecules on the substrate surface. In this case, the specific antibodies must be immobilized or coated on the culture substrate surface beforehand by a physical method such as adsorption or a chemical method such as covalent bonding. For example, for a recombinant protein obtained by fusing the IgG Fc region to the adhesion molecule, the antibody attached to the culture substrate beforehand may be one that specifically recognizes the IgG Fc region. For a recombinant protein obtained by fusing a protein or tag sequence peptide to the adhesion molecule, an antibody specific for the fused molecule may be attached to the culture substrate beforehand for use.

The adhesion molecule immobilized or coated on the solid phase surface of a cell culture substrate for carrying out the invention may be of a single type, or two or more different adhesion molecules may be used in combination. In such cases, solutions of each adhesion molecule may be mixed and the mixed solution applied in the manner described above.

The concentration of the adhesion molecule solution must be appropriately considered based on the adsorption and/or affinity of the molecule and the physical properties of the molecule, but for a recombinant protein obtained by fusion of an Fc region with the extracellular region of E-cadherin, the concentration is about 0.01-1000 µg/mL, preferably about 0.1-200 µg/mL, even more preferably 1-50 µg/mL and most preferably 5-10 µg/mL.

The pluripotent stem cells used to carry out the invention are seeded on a culture substrate prepared in the manner described above. The culturing method and culturing conditions for the pluripotent stem cells may be an ordinary culturing method and culturing conditions for pluripotent stem cells, except for using the culture substrate described above. Ordinary culturing methods and culturing conditions for pluripotent stem cells are described in the literature mentioned above, and specifically, Guide to Techniques in Mouse Development (Wasserman et al. eds., Academic Press, 1993); Embryonic Stem Cell Differentiation in vitro (M. V. Wiles, Meth. Enzymol. 225:900, 1993); Manipulating the Mouse Embryo: A Laboratory Manual (Hogan et al. eds., Cold Spring Harbor Laboratory Press, 1994); Embryonic Stem Cells (Turksen ed., Humana Press, 2002), as well as other sources (Matsui et al., Cell 70:841, 1992. Thomson et al., U.S. Pat. No. 5,843,780; Thomson et al., Science 282.114, 1998; Shamblott et al., Proc. Natl. Acad. Sci. USA 95:13726, 1998; Shamblott et al. U.S. Pat. No. 6,090,622; Reubinoff et al., Nat. Biotech. 18:399, 2000; and International Patent Publication No. WO00/27995), although there is no particular restriction to these.

The liquid medium used for the culturing of the pluripotent stem cells may be any one that can be employed in conventional methods of passaging pluripotent stem cells. As specific examples, there may be mentioned Dulbecco's Modified Eagle's Medium (DMEM), Glasgow Minimum Essential Medium (GMEM), RPMI1640 medium and the like, usually with addition of about 2 mM of glutamine and/or about 100 µM of 2-mercaptoethanol. There may also be used KnockOut DMEM (Invitrogen), ES cell-qualified DMEM (Cell & Molecular Technologies) and TX-WES (Thromb-X), which are commercially available as ES cell culturing media. Such media preferably contain FBS added to about 5-25%, but they may also be serum-free media, substituted with, for example, 15-20% KnockOut Serum Replacement (Invitrogen). MEF cell culture supernatant or medium containing added bFGF/FGF-2, SCF and the like may also be used, and detailed procedures therefor are publicly known (Xu et al., Nature Biotech. 19:971, 2001; International Patent Publication No. WO01/51616; International Patent Publication No. WO03/020920; Amit et al., Biol. Reprod., 70:837, 2004).

The liquid medium for culturing of the pluripotent stem cells also preferably has substances and factors added thereto which help maintain the undifferentiated state of the pluripotent stem cells. The specific substances and factors are not particularly restricted, but LIF is preferred for murine ES/EG cells. LIF is a protein factor that is publicly known from the published literature (Smith & Hooper, Dev. Biol. 121:1, 1987; Smith et al., Nature 336:688, 1988; Rathjen et al., Genes Dev. 4:2308, 1990), as well as by Access Nos. X13967 (human LIF), X06381 (murine LIF) and NM_022196 (rat LIF), and its recombinant proteins can be obtained, for example, under the trade name of ESGRO (Chemicon). Addition of GSK-3 inhibitor to the culture medium can efficiently maintain the undifferentiated state of murine and human ES cells without addition of other growth factors or bioactive factors (Sato et al., Nature Med. 10:55, 2004). In this case, any substance having activity of inhibiting GSK-3 activity may be used, and there may be mentioned, for example, the Wnt family of molecules (Manoukian & Woodgett, Adv. Cancer Res. 84:203, 2002; Doble & Woodgett, J. Cell Sci. 116: 1175, 2003).

By seeding pluripotent stem cells that have been maintained through passaging by conventional methods on culture substrate prepared by the method described above and culturing with the aforementioned culturing conditions and method for carrying out the invention, it is possible to accomplish passaging with the cells in a dispersed state, while maintaining the original undifferentiated state of the cells. Since the pluripotent stem cells cultured in this state are not physically inhibited during cell division, and/or the cell growth-inhibiting mechanisms mediated by intercellular contact do not function, and/or cell survival is increased and the dead cell count is decreased, significant cell proliferation and growth is observed. In the case of culturing of murine ES cells by the method of the invention, as one example, it is possible to achieve a proliferation rate of at least 1.25 times, preferably at least 1.5 times and more preferably at least 2 times compared to culturing by a conventional method. Passaging to about 4 generations under these conditions allows recovery of at least 3 times, and preferably at least 10 times, the number of cells recovered by conventional methods. The proliferation rate may be indicated by indices such as the cell count increase rate or doubling speed per unit of time, and the methods of measurement and calculation used may be any publicly known methods employed for common cell experiments.

As explained above, the state of undifferentiation of pluripotent stem cells means that the pluripotent stem cells are capable of prolonged or virtually indefinite proliferation and exhibit normal karyotype (chromosomes), while having the capacity to differentiate into all three germ layers under the appropriate conditions. Also, they preferably have at least one of the other properties of pluripotent stem cells such as telomerase activity maintenance, teratoma formation, or ability to form chimeras. Methods of examining cell character and properties may be easily carried out using established standard protocols with reference to the literature cited above such as, for example, Guide to Techniques in Mouse Development (Wasserman et al. eds., Academic Press, 1993); Embryonic Stem Cell Differentiation in vitro (M. V. Wiles, Meth. Enzymol. 225:900, 1993); Manipulating the Mouse Embryo: *A Laboratory Manual* (Hogan et al. eds., Cold Spring Harbor Laboratory Press, 1994); or Embryonic Stem Cells (Turksen ed., Humana Press, 2002), but there is no particular restriction to these methods.

Pluripotent stem cells in an undifferentiated state may be defined as cells for which at least one and preferably more marker molecules can be confirmed by at least one, and preferably more than one, of the methods described below. Expression of various markers specific to undifferentiated pluripotent stem cells is detected by conventional biochemical or immunochemical methods. Although there are no particular restrictions on the method employed, immunochemical methods such as immunohistological staining or immunoblot analysis are preferred. There may be utilized, in such methods, marker-specific polyclonal antibodies or monoclonal antibodies that bind to undifferentiated pluripotent stem cells. Antibodies that target individual specific markers are commercially available and may be conveniently used. Specific markers for undifferentiated pluripotent stem cells include ALP activity and Oct-3/4 or Rex-1/Zfp42 gene product expression. Various antigenic molecules may also be used, which include the undifferentiation markers SSEA-1 for murine ES cells, SSEA-3 for human ES cells, or SSEA-4, TRA-1-60, TRA-1-81 gCTM-2 and the like. Expression of them is reduced or eliminated upon differentiation of ES cells.

Alternatively, expression of undifferentiated pluripotent stem cells markers can be confirmed by molecular biological methods employed often in the prior art for amplification, detection and analysis of mRNA coding for desired marker proteins, such as reverse transcriptase polymerase chain reaction (RT-PCR) or hybridization analysis, without regard to the particular method. Nucleic acid sequences for genes coding for marker proteins specific to undifferentiated pluripotent stem cells (for example, Oct-3/4, Rex-1/Zfp42 or Nanog) are known, and marker-specific sequences necessary as primers or probes can be easily determined working from public databases such as NCBI.

Use as Gene Transfer Method into Pluripotent Stem Cells

According to another mode of the invention, the method disclosed by the invention may be used as a method for efficient transfer of a desired exogenous gene into pluripotent stem cells. There are no particular restrictions on the exogenous gene to be transferred, and for example, it may be for a natural protein such as a growth factor or receptor, an enzyme, a transcription factor or the like, or an artificial protein generated by modification using a genetic engineering method. The transferred gene may also be functional RNA such as a ribozyme or siRNA. The exogenous gene may even be a marker gene for evaluation of gene transfer efficiency or expression stability, such as a gene coding for GFP (Green Fluorescent Protein) or β-galactosidase, luciferase or the like.

As one preferred mode, the exogenous gene to be transferred is linked to a nucleic acid sequence that allows transcription and expression of the gene, i.e., a promoter sequence, under control of the promoter in a form allowing its transcription and expression. In such cases the gene is also preferably linked to a polyA signal sequence. As promoters that allow transcription and expression of exogenous genes in pluripotent stem cells, there may be mentioned promoters from viruses such as SV40 virus, CMV or Rous sarcoma virus, or β-actin promoter, EF1α promoter or the like. Depending on the purpose, there may also be used a nucleic acid sequence allowing transcription or expression of a specific gene in certain cell/tissue types or in cells of a given stage of differentiation, i.e., a cell/tissue-specific promoter sequence or differentiation stage-specific promoter, or Pol. III promoter for RNA expression. These promoter sequences may be utilized from public DNA databases such as NCBI, and ordinary molecular biological techniques may be employed to construct gene vectors comprising desired gene sequences. Vectors for these promoters may be obtained from Invitrogen, Promega, Ambion and elsewhere.

The method for introducing the gene (vector) is not particularly restricted, and there may be mentioned, for example, transfection methods using calcium phosphate or DEAE-dextran. Transfection methods for cell targets of the gene transfer can also be applied using lipid preparations that can be taken up into the cells and have low cytotoxicity, such as LipofectAMINE (Invitrogen), Superfect (Qiagen) or DOTMA (Roche), to form liposome-nucleic acid complexes containing the target gene. Alternatively, the gene of interest may be incorporated into a viral vector such as a retrovirus or adenovirus and the recombinant virus used to infect the cells. In this case, the viral vector is a re-construct of the nucleic acid sequence of full-length or partially deficient or mutated viral DNA or RNA, with the gene of interest incorporated in an expressible manner.

Use of Pluripotent Stem Cells Grown by Method of the Invention

The pluripotent stem cells that have been grown by the growing method according to the invention may then be obtained efficiently and in large amounts as pluripotent stem cells maintaining their undifferentiated state, using publicly known cell recovery methods. The gene transfer method of the invention allows efficient and high-yield production of pluripotent stem cells having the desired gene transferred and expressed therein. The pluripotent stem cells obtained in this manner will hereinafter be referred to as "pluripotent stem cells prepared according to the invention".

As methods of recovering pluripotent stem cells there may be mentioned methods using publicly known enzyme treatment, which are ordinarily employed for passaging of pluripotent stem cells. As a specific example, there may be mentioned a method wherein the medium is removed from a culturing vessel in which pluripotent stem cells have been cultured, PBS is used for rinsing several times, preferably 2-3 times, a solution containing an appropriate protease (for example, a solution containing a protease such as trypsin or dispase) is added, culturing is carried out at 37° C. for an appropriate period, preferably about 1-20 minutes and more preferably 3-10 minutes, and then the mixture is suspended in an appropriate solution such as the aforementioned ES cell culturing medium to obtain single cells. Non-enzymatic methods may also be used, and for example, there may be mentioned a method wherein the medium is removed from a culturing vessel in which pluripotent stem cells have been cultured, PBS is used for rinsing several times, preferably 2-3 times, an ethylenediamine tetraacetate (EDTA) solution is added to a final concentration of 0.01-100 mM, preferably 0.1-50 mM and more preferably 1-10 mM, for treatment at 37° C. for an appropriate time, preferably about 1-60 minutes and more preferably 10-30 minutes for detachment of the cells, and then the mixture is suspended in an appropriate solution such as the aforementioned ES cell culturing medium to obtain individual cells. The same method may also be carried out using ethyleneglycol bis(2-aminoethylether) tetraacetate (EGTA) instead of EDTA.

The present invention also provides differentiated cells produced by appropriate differentiation-inducing treatment from pluripotent stem cells prepared according to the invention. The differentiated cells are not particularly restricted as long as they are of a cell type whose differentiation can generally be induced from pluripotent stem cells. Specifically, there may be mentioned ectodermal cells or ectoderm-derived cells, mesodermal cells or mesoderm-derived cells, endodermal cells or endoderm-derived cells, and the like.

Ectoderm-derived cells are cells composing tissues and organs such as neural tissue, the pineal body, the adrenal medulla, plastids and epidermal tissue, but they are not limited to these. Mesoderm-derived cells are cells composing tissues and organs such as muscle tissue, connective tissue, bone tissue, cartilage tissue, cardiac tissue, vascular tissue, blood tissue, dermal tissue, urinary organs and reproductive organs, but they are not limited to these. Endoderm-derived cells are cells composing tissues and organs such as digestive tract tissue, respiratory organs, or thymus, thyroid, parathyroid, bladder, middle ear, liver and pancreas tissue, but they are not limited to these.

The pluripotent stem cells prepared according to the invention and/or differentiated cells prepared from such cells are useful for pharmacological evaluation or activity evaluation of various physiologically active substances (such as drugs) or novel gene products of unknown function. For example, they may be utilized for screening of substances and drugs involved with functional regulation of pluripotent stem cells or various differentiated cells, and/or substances or drugs with toxicity or inhibitory action on pluripotent stem cells or various differentiated cells. Currently, very few screening methods have been established using human cells, and differentiated cells derived from pluripotent stem cells prepared according to the invention are useful cell sources for conducting such screening methods.

The invention also relates to a method of generating a chimeric embryos or chimeric animals using pluripotent stem cells prepared by the method disclosed by the invention, and to the generated chimeric embryos and chimeric animals. Standard protocols have already been established for generating chimeric embryos and chimeric animals, and they can be easily generated with reference to, for example, Manipulating the Mouse Embryo: *A Laboratory Manual* (Hogan et al. eds., Cold Spring Harbor Laboratory Press, 1994), though there is no particular limitation to this reference.

EXAMPLES

The present invention will now be explained in greater detail by the following examples, with the understanding that these are only examples for the invention and are not intended to restrict its scope in any way.

Example 1

Preparation of Recombinant E-Cadherin Protein

The methods for construction of a vector for expression of a fusion protein comprising the murine E-cadherin extracellular region and IgG Fc portion (IgG/Fc) (hereinafter referred to as "E-cad-Fc"), and for production and purification of the protein were based on methods reported by the present inventors (Nagaoka et al., Biotechnol. Lett. 24:1857, 2002 (Non-patent document 6); Protein Eng. 16:243, 2003 (Non-patent document 7)). First, an extracellular domain (E-cad-ECD)-coding DNA fragment (corresponding to amino acid residues 1-699) from E-cadherin cDNA was amplified using as template cDNA containing the full-length sequence for murine E-cadherin (allotted by RIKEN; RDB No. 1184) as template. A DNA fragment coding for murine IgG/Fc was isolated from cDNA obtained by preparing mRNA from a murine IgG1-expressing hybridoma and performing reverse transcription with Reverse Transcriptase. After confirming the nucleotide sequences of both DNA fragments, they were incorporated into expression vector pRC-CMV (Invitrogen) to construct expression vector pRC-E-cad-Fc containing the E-cad-ECD and IgG/Fc sequences.

CHO-K1 cells (obtained from RIKEN, Tsukuba) were used for production of E-cad-Fc protein. The linearized pRC-E-cad-Fc (1.0 µg) was mixed with 5.0 µL of LipofectAMINE™ reagent (Invitrogen), and used for gene transfer into the CHO-K1 cells according to the protocol recommended in the product manual. Next, in order to obtain a cell clone producing the E-cad-Fc protein constitutively and in large amounts, the cells were recovered after the second day from gene transfer and seeded at 0.2 cells per well in a 96-well plate (IWAKI). After culturing for 7 days in RPMI 1640 containing 400 µg/mL of G418 (Invitrogen), the culture supernatants were collected from wells with surviving cells and the E-cad-Fc protein contents in the culture supernatants were measured. Clones with the highest E-cad-Fc protein production (4G7 lines) were isolated and used for the following experiment. These cells were conditioned in serum-free medium (CHO-S-SFM II; Invitrogen) and then mass cultured using a spinner flask, and the culture supernatant was collected.

The culture supernatant was filtered with a 0.45 µm membrane filter, and then concentrated using a 100 kDa-pore size ultrafiltration membrane (YM100; Amicon) and a stirred cell (Amicon 8200; Amicon). The concentrated solution was dialyzed with 20 mM phosphate buffer (pH 7.2) and then purified by an ordinary method using a Protein A column (Amersham Biosciences) and supplied for the following experiment.

Example 2

Adhesion of ES Cells to E-Cad-Fc Plate

The adhesion of ES cells to a cell culturing plate coated with the E-cad-Fc protein (hereunder, "E-cad-Fc plate") was examined. A PBS-diluted solution of the E-cad-Fc protein was poured into untreated polystyrene culturing plates of different sizes and treated for coating overnight at 37° C. After rinsing and before seeding of the cells, blocking treatment was performed for 1-2 hours with 0.1% BSA solution to prevent non-specific adhesion of the cells. As a control, plates coated with BSA (0.1%), gelatin (0.1%), type I collagen (0.01%; KOKEN) or fibronectin (5.0 µg/mL; KOKEN) were used.

The ES cell lines used were EB3 cells (provided by Prof. Hitoshi Niwa of RIKEN), R1 cells (Nagy et al., Proc. Natl. Acad. Sci. USA 90:8424, 1993) and 129SV cells (obtained from Dainippon Pharmaceutical Co. Ltd.), and the experimental results showed no differences between the different ES cell lines. These ES cells were passaged according to the methods described in Manipulating the Mouse Embryo: A Laboratory Manual (Hogan et al. eds., Cold Spring Harbor Laboratory Press, 1994) and Embryonic Stem Cells: Methods and Protocols (Turksen ed., Humana Press, 2002), using KnockOut-DMEM (Invitrogen) medium containing 10% FBS, 0.1 mM MEM non-essential amino acid solution, 2 mM L-glutamine and 0.1 mM 2-mercaptoethanol (hereinafter referred to as ESM), with addition of 1000 U/mL LIF (ES-GRO; Chemicon), while maintaining their undifferentiated states, and they were supplied for experimentation. The ES cells passaged under these conditions will hereinafter be referred to as "ES cells passaged under ordinary conditions".

The ES cells passaged under ordinary conditions were rinsed twice with serum-free medium and treated with 0.25% trypsin solution containing 1 mM EDTA to obtain single cells, which were suspended in ESM. Unless otherwise specified, the same conditions were used thereinafter for detachment of the ES cells from the plate, passaging and other experiments. The purified E-cad-Fc protein was coated onto an untreated 96-well plate (IWAKI) by the method described above, and the cell suspension prepared at $3.0 \times 10^5$ cells/mL was seeded therein at 100 µL and cultured for 4 hours. After rinsing with serum-free medium, the medium was replaced with medium containing 10% Alamar Blue (Biosource International) for 4 hours of reaction, after which the absorbance was measured as an index of the viable cell count.

The results are shown in FIG. 1. ES cells generally have low adhesion abilities compared to fibroblasts and epithelial cells, and they essentially fail to adhere onto a polystyrene plate that is either untreated or coated with BSA, and they form an aggregated cell mass in the medium; however, after pretreatment of the culturing plate with gelatin, collagen or fibronectin, they are able to adhere in the same way as when seeded on an ordinary cell culturing plate. When the adhesion ability of ES cells was examined using a coated plate with different E-cad-Fc concentrations, both the R1 cell line and EB3 cell line exhibited satisfactory adhesion with concentrations of 5.0 µg/mL and above. Incidentally, ES cells are also capable of adhering to an E-cad-Fc plate under serum-free conditions, and the adhesion to the plate is clearly independent of adhesion molecules in the serum such as fibronectin.

Binding via E-cadherin is known to be $Ca^{2+}$ dependent (Mareel et al., Int. J. Dev. Biol. 37:227, 1993; Takeichi, Curr. Opin. Cell Biol. 7: 619, 1995; Marrs & Nelson, Int. Rev. Cytol. 165:159, 1996). In order to examine the effect of chelating agent addition on adhesion of ES cells to the E-cad-Fc plate, ES cells cultured for 4 hours on an E-cad-Fc plate in the same manner were treated for 30 minutes with ethylenediamine tetraacetate (EDTA) or ethyleneglycol bis(2-aminoethylether)tetraacetate (EGTA) at a 5 mM final concentration, and after rinsing the cells with PBS, the cell counts were measured with Alamar Blue in the same manner as above. With treatment using EDTA which has low metal ion selectivity, adhesion of the ES cells to both E-cad-Fc and fibronectin was detached, but with treatment using EGTA which has high $Ca^{2+}$ selectivity, binding with fibronectin was not inhibited and only binding with E-cadherin was specifically detached. This effect was not prevented even with addition of 5 mM $Mg^{2+}$ for the EGTA treatment. These results suggest that adhesion of ES cells to an E-cad-Fc plate involves interaction between E-cadherin molecules present on the surfaces of the ES cells and E-cadherin molecules immobilized on the solid phase surface of the E-cad-Fc plate.

Figure 2:
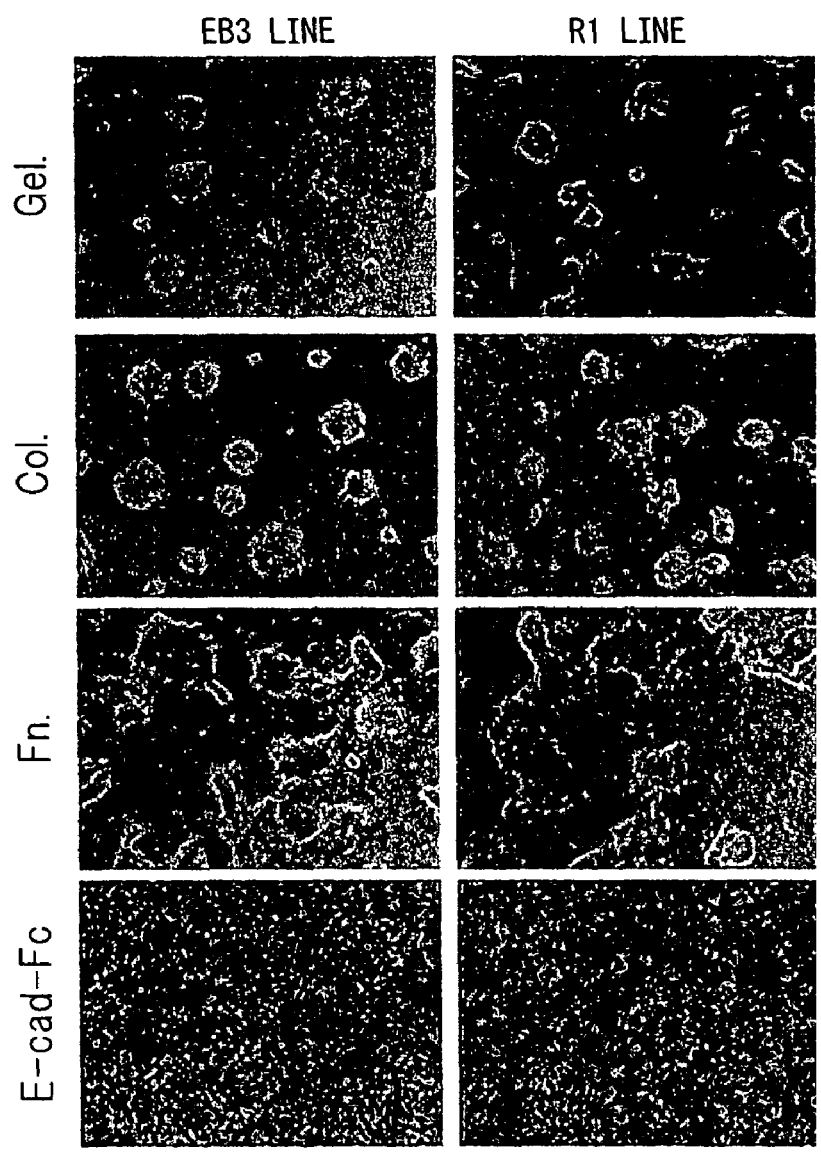
FIG. 2 is a set of photographs showing the morphology of ES cells seeded on an E-cad-Fc plate. The cell images were taken two days after seeding the ES cells on a plate coated with gelatin, type I collagen, fibronectin or E-cad-Fc (indicated by Gel., Col., Fn. and E-cad-Fc, respectively).

Next, ES cells passaged under ordinary culturing conditions were seeded in an E-cad-Fc plate or a 24-well plate (IWAKI) coated with another substrate, and culturing was carried out. It is known that ES cells generally form tight, rounded colonies on feeder cells or on an ordinary cell culturing plate. Here, ES cells formed the same kind of distinct, tight colonies even with an untreated polystyrene culturing plate coated with gelatin, type I collagen or fibronectin (see FIG. 2). However, it is of note that ES cells seeded on the E-cad-Fc plate, whether EB3 cells or R1 cells, essentially failed to form distinct colonies even 2 or 3 days after seeding, and they were instead observed to increase in number as individually dispersed cells.

Example 3

Culturing of ES Cells Using E-Cad-Fc Plate

Figure 3A:
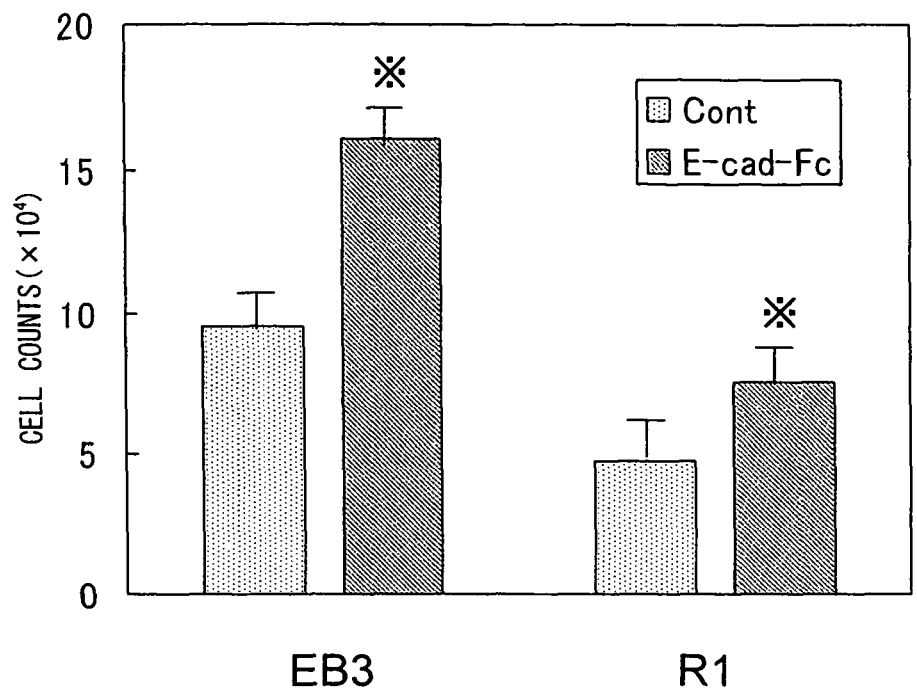
FIG. 3A is a graph showing the proliferation potency of ES cells seeded on an E-cad-Fc plate. The ES cells were seeded on a gelatin plate (indicated as Cont) or an E-cad-Fc plate, and the cell counts on the third day were compared. *: with respect to Cont group, $p<0.01$.

In order to examine the proliferation potency of ES cells on an E-cad-Fc plate, ES cells passaged under ordinary conditions were recovered and 500 of the ES cells were seeded on an E-cad-Fc plate or a gelatin plate (96-well plate) and cultured for 3 to 4 days. After rinsing the cells with serum-free medium, the cell counts were measured with Alamar Blue in the same manner as above. As a result, the number of ES cells cultured on the E-cad-Fc plate with respect to the number of ES cells cultured on the gelatin plate by day 3 of culturing was significantly higher for both the EB3 and R1 cell lines (see FIG. 3A). Also, the cell counts of the E-cad-Fc plate groups with both ES cell lines were approximately 2 times greater by day 4 of culturing. When the ES cells were recovered after four similar passages and the counts were recorded, the numbers of E-cad-Fc plate-cultured ES cells were more than 3-5 times greater than those cultured on the ordinary gelatin plate. There was no difference between the plates in terms of the adhesion rate immediately after seeding of the ES cells, suggesting that ES cells cultured on an E-cad-Fc plate have higher proliferation potency and survival ability. When the same experiment was conducted with F9 cells, no difference was found in the cell proliferation potencies of the E-cad-Fc plate cultured group and the ordinary plate cultured group.

Figure 3B:
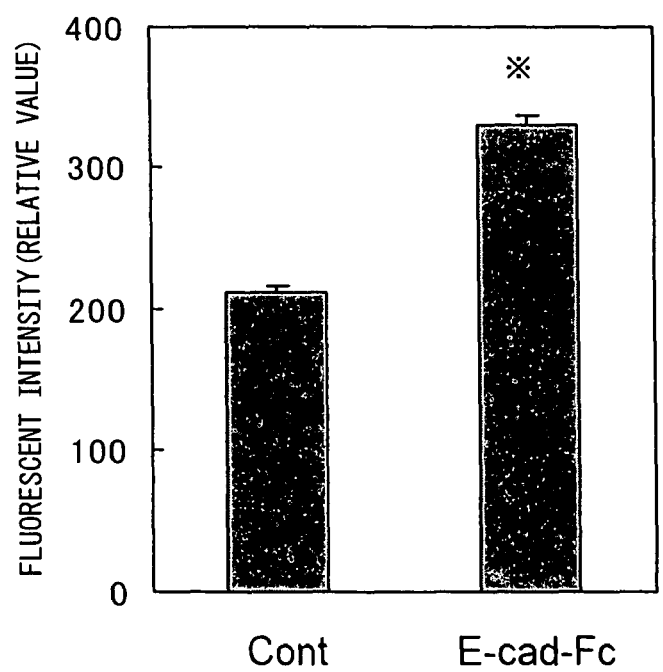
FIG. 3B is a graph showing BrdU uptake by ES cells seeded on an E-cad-Fc plate. The ES cells (EB3) were seeded on a gelatin plate (indicated as Cont) or an E-cad-Fc plate, and labeled with BrdU. The BrdU taken up into the cells after three days was detected by antibody staining using a fluorescent dye. *: with respect to Cont group, $p<0.01$.

Next, the DNA synthesis of the ES cells was examined using uptake of 5-bromo-2'-deoxyuridine (BrdU) as the index. ES cells cultured for 3 days under the conditions described above were recovered as single cells after labeling with BrdU (10 µM) for 30 minutes, and were re-seeded in a 96-well plate. After 4 hours, the attached ES cells were fixed with FixDenat solution (Roche Applied Science) and rinsed with PBS, after which they were reacted with anti-BrdU antibody (BMG 6H8; Roche Applied Science) (100-fold dilution) and dyed using cyanogen 3 (Cy3)-labeled antibody (Jackson Immunoresearch Laboratory) (1:1000 dilution). The cell nuclei were stained with 4',6-diamidino-2-phenylindole (DAPI) solution (0.1 µg/mL). The antibody and dye stain images were observed using an ArrayScan™ system (Cellomics). As a result, the E-cad-Fc plate-cultured group exhibited significantly higher BrdU uptake compared to the ordinary plate-cultured group (see FIG. 3B).

It is known that ES cells generally undergo spontaneous differentiation after forming large, close colonies. Thus, when the three different murine ES cell lines used in this experiment are cultured on an ordinary plate, the colonies grow excessively large and produce differentiated cells with different morphologies unless they are passaged every 2 or 3 days. When cultured on an E-cad-Fc plate, however, it was sufficient to passage only about once ever 5-7 days if the initial seeding count was reduced, and no excessive colony formation or differentiated cells was observed under these culturing conditions. Therefore, in order to confirm whether the ES cells cultured on E-cad-Fc plate maintained their undifferentiated state or whether the dispersed state and undifferentiated state of the ES cells were maintained even after multiple passaging, they were passaged several times on the plate, and the properties of the resulting ES cells were examined.

First, ALP activity and Oct-3/4 protein expression were examined as indices of undifferentiated ES cells, in order to confirm the differentiated state of the ES cells. ALP activity was detected using a Sigma Diagnostics Alkaline Phosphatase Kit (Sigma). After rinsing the cultured ES cells (EB3 cell and R1 cell lines) with PBS, they were fixed with citrate solution containing 66% acetone/3% formalin and rinsed with PBS, after which they were treated for 15 minutes with naphthol AS-BI phosphate alkaline staining solution included with the kit for color reaction (see FIG. 4A).

Oct-3/4 protein expression was examined by immunostaining. Specifically, cultured ES cells were fixed with 8% formaldehyde (Wako Pure Chemical Industries Co., Ltd.) and rinsed with PBS, and then reacted with anti-Oct-3/4 antibody (product of Santa Cruz)(1:200 dilution) and dyed with Alexa Fluor-labeled antibody (Alexa-488; Molecular Probes)(1:1000 dilution). The cell nuclei were stained with DAPI solution (0.1 µg/mL). The antibody and dye stain images were observed under a fluorescent microscope (see FIG. 4B).

As a result, high ALP activity (FIG. 4A) and Oct-3/4 protein expression (FIG. 4B) were confirmed with the ES cells cultured for 14 days on the E-cad-Fc plate, similarly to ES cells cultured on a plate coated with gelatin used as a control group (hereinafter, "gelatin plate").

Expression of Oct-3/4 and Rex-1/Zfp42 genes as undifferentiated ES cell markers was examined next. ES cells cultured on an E-cad-Fc plate or gelatin plate for 14 days were recovered and total RNA was prepared using 1 ml of TRIZOL (Invitrogen). Next, cDNA was synthesized by a common method using M-MLV reverse transcriptase (Invitrogen), and this was used as a template for the polymerase chain reaction (PCR) using the following primers for amplification of each gene fragment.

```
Oct-3/4 [amplification size: 528 bp]
5'-primer:
5'-GAAGTTGGAGAAGGTGGAACC-3'        (SEQ ID NO: 3)

3'-primer:
5'-GCCTCATACTCTTCTCGTTGG-3'        (SEQ ID NO: 4)

Rex-1 [amplification size: 930 bp]
5'-primer:
5'-AAAGTGAGATTAGCCCCGAG-3'         (SEQ ID NO: 5)

3'-primer:
5'-TCCCATCCCCTTCAATAGCA-3'         (SEQ ID NO: 6)

Nanog [amplification size: 710 bp]
5'-primer:
5'-GAGGAAGCATCGAATTCTGG-3'         (SEQ ID NO: 7)

3'-primer:
5'-AAGTTATGGAGCGGAGCAGC-3'         (SEQ ID NO: 8)

GAPDH (glyceraldehyde-3-phosphate dehydrogenase)
[amplification size: 858 bp]
5'-primer:
5'-GGAAGCTTGTCATCAACGG-3'          (SEQ ID NO: 9)

3'-primer:
5'-CTCTTGCTCAGTGTCCTTGC-3'         (SEQ ID NO: 10)
```

PCR was carried out using a TaKaRa PCR Thermal Cycler MP (TaKaRa), with TaKaRa Taq (TAKARA) as a thermostable DNA polymerase. First, the cDNA-containing PCR reaction solution was heated at 94° C. and then a heating cycle of 94° C.: 30 seconds→59° C.: 30 seconds→72° C.: 60 seconds was repeated 22 times, followed by final heating at 72° C. for 5 minutes and then cooling to 4° C. The PCR product was electrophoresed on 1.5% agarose gel, dyed with SYBR Green I (TAKARA) and detected with Typhoon 8600 (Amersham Biosciences).

Figure 5:
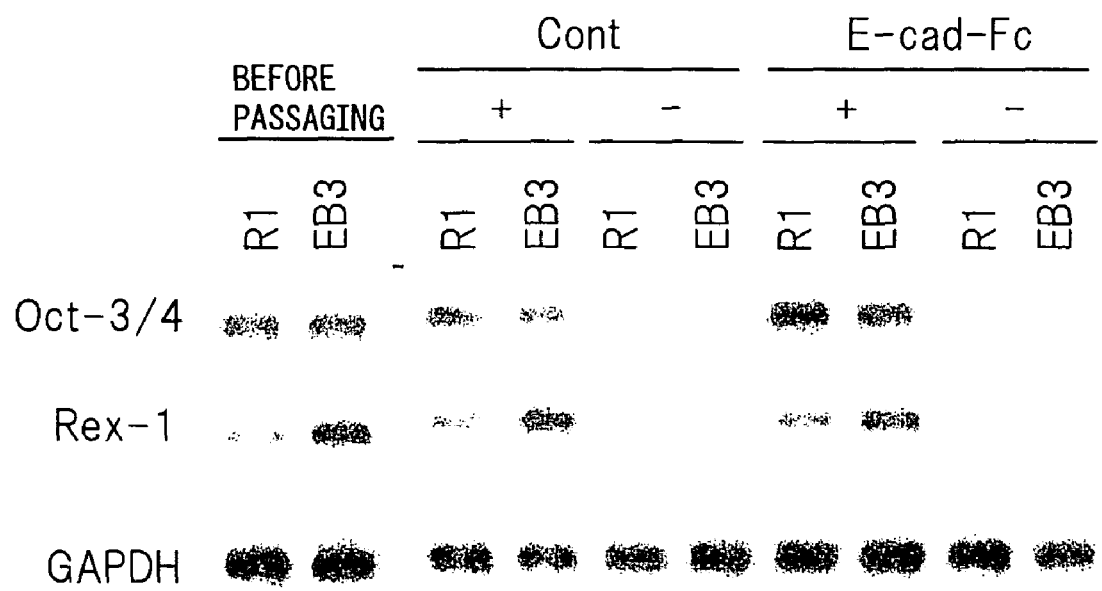
FIG. 5 is a set of photographs showing expression of markers for undifferentiated ES cells seeded on an E-cad-Fc plate. The ES cells were seeded on a gelatin plate (indicated as Cont) or an E-cad-Fc plate, and Oct-3/4 and Rex-1 gene expressions were examined by RT-PCR on the 14th day. The + and − symbols in the figure respectively represent addition and non-addition of LIF to the culturing medium.

The results are shown in FIG. 5. The ES cells cultured on the ordinary gelatin plate showed high expression of Oct-3/4, Rex-1 and Nanog in the presence of LIF, with significant reduction of expression in the absence of LIF. Similar results were found with the ES cells cultured on the E-cad-Fc plate, with high expression of Oct-3/4, Rex-1 and Nanog being exhibited in the presence of LIF. The same samples were used to examine expression of differentiation marker genes for neurons, mesodermal cells and endodermal cells, such as NeuroD3 or Sox-1, T/Brachyury, Flk-1, hemoglobin, α-fetoprotein and transthyretin, but no differentiation marker gene expression was found in the presence of LIF, for ES cells cultured on either the gelatin plate or the E-cad-Fc plate. As seen by the results in FIGS. 4A, 4B and 5, it was confirmed that the E-cad-Fc plate-cultured ES cells proliferated without forming colonies and exhibited a different morphology than by ordinary culturing, yet while maintaining their undifferentiated state.

It was then examined whether or not the reactivity of E-cad-Fc plate-cultured ES cells for LIF had been altered. ES cells passaged on an ordinary gelatin plate and on an E-cad-Fc plate were cultured for 5 days with a 0-1000 U/mL LIF concentration without passaging, and then both groups of cells were reseeded on a gelatin plate and cultured for another 3 days (with a constant LIF concentration during the culturing period). The ALP activity of the ES cell colonies formed on the plates was detected by the same method described above, and the proportion of colonies maintaining an undifferentiated state was measured. Colonies with ALP activity found in at least 80% of the cells were judged as being "undifferentiated".

Figure 6:
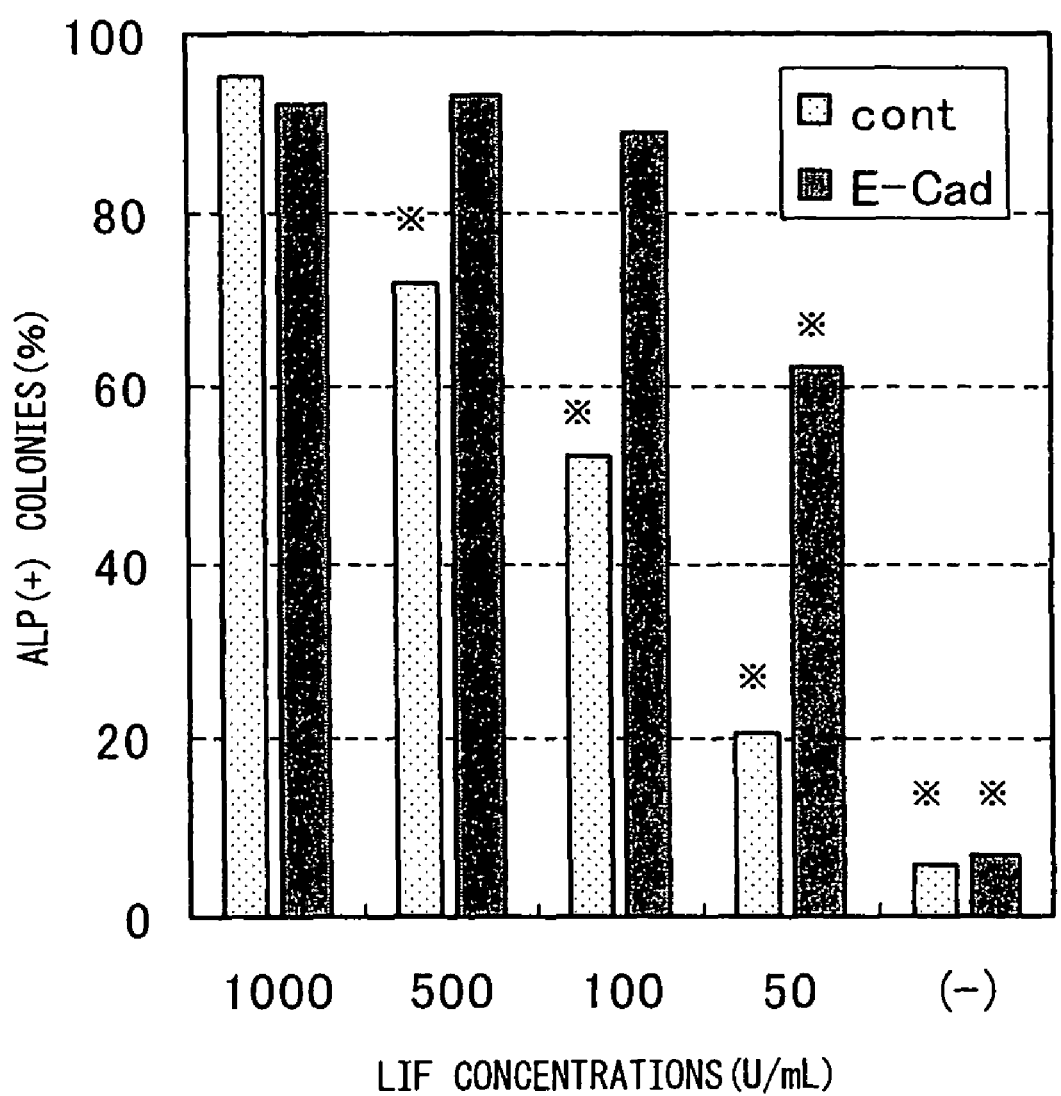
FIG. 6 is a graph showing the LIF reactivity of ES cells seeded on an E-cad-Fc plate. The ES cells (R1 line) were seeded on a gelatin plate (indicated as Cont) or an E-cad-Fc plate and cultured with different concentrations of LIF to from colonies, and the ALP activity was detected for measurement of the proportion of "undifferentiated" colonies. *: with respect to Cont/LIF 1000 U/mL, $p<0.05$.

The ES cells cultured on the gelatin plate had formed oversized colonies by the end of the first 5 days of culturing, but no cells were observed that could be clearly judged to be differentiated cells. The ES cells cultured on the E-cad-Fc plate proliferated without forming colonies and maintained their dispersed state, as in the previous experiment. After reseeding, the ES cells cultured on the ordinary plate with 1000 U/mL LIF concentration maintained ALP activity in virtually all of the colonies, but the proportion of undifferentiated colonies decreased with lower LIF concentration (see FIG. 6). The ES cells cultured on the E-cad-Fc plate beforehand were able to maintain undifferentiated characteristics in virtually all of the colonies, even with an LIF concentration of 100 U/mL. No inhibition of proliferation potency with lower LIF concentration was found. This suggested that culturing with an E-cad-Fc plate allows the amount of additional factors necessary for ES cell growth, such as LIF, to be reduced compared to the prior art methods.

It was next examined whether or not an E-cad-Fc plate can be used for feeder-independent conditioning of ES cells. ES/EG cells are usually passaged and maintained by co-culturing with feeder cells, but their feeder-dependent culturing state can be conditioned to a feeder-independent state. However, this requires a high density of ES cells and repeated passaging in medium containing a high concentration of LIF (normally about 5- to 10-fold). For example, in order for ES cells (R1 line) grown in a feeder-dependent state to be conditioned to a feeder-independent state, it is necessary to seed at a cell density of about $5.0 \times 10^4$ cells/cm$^2$ and add LIF at $1 \times 10^4$ U/mL. However, it was possible to condition ES cells to a feeder-independent state as in the prior art by seeding ES cells on an E-cad-Fc plate at a cell density of 500 cells/cm$^2$ and passaging with ESM containing $1 \times 10^3$ U/mL LIF. It was also confirmed that ES cells prepared in this manner adequately retained their undifferentiated state and pluripotency.

Example 4

Examination of Differentiating Ability of ES Cells Cultured on E-cad-Fc Plate

It was confirmed that ES cells passaged multiple times on an E-cad-Fc plate still have pluripotency. First, the ES cells were suspension cultured in the absence of LIF to form an embryoid bodies (EB), and the progression of spontaneous differentiation was examined based on expression of several differentiation marker genes. Specifically, in order to form an EB from the ES cells, ES cells passaged at least 3 times on an E-cad-Fc plate were recovered in the form of single cells, and then a droplet containing 500 cells was prepared in 15 µL of LIF-free ESM for hanging-drop culture. The EB formed in the hanging-drop culture was periodically collected and RNA preparation and cDNA synthesis were accomplished by the same methods described above. RT-PCR reaction was conducted with this cDNA as template using the following primers, for amplification of each marker gene fragment.

```
NeuroD3 [amplification size: 405 bp]
5'-primer:
5'-CATCTCTGATCTCGACTGC-3'        (SEQ ID NO: 11)

3'-primer:
5'-CCAGATGTAGTTGTAGGCG-3'        (SEQ ID NO: 12)

Sox-1 [amplification size: 407 bp]
5'-primer:
5'-GCACACAGCGTTTTCTCGG-3'        (SEQ ID NO: 13)

3'-primer:
5'-ACATCCGACTCCTCTTCCC-3'        (SEQ ID NO: 14)

T/Brachyury [amplification size: 528 bp]
5'-primer:
5'-TCCAGGTGCTATATATTGCC-3'       (SEQ ID NO: 15)

3'-primer:
5'-TGCTGCCTGTGAGTCACAAC-3'       (SEQ ID NO: 16)

Flk-1 [amplification size: 398 bp]
5'-primer:
5'-TAGGTGCCTCCCCATACCCTGG-3'     (SEQ ID NO: 17)

3'-primer:
5'-TGGCCGGCTCTTTCGCTTACTG-3'     (SEQ ID NO: 18)

hemoglobin [amplification size: 415 bp]
5'-primer:
5'-AACCCTCAATGGCCTGTGG-3'        (SEQ ID NO: 19)

3'-primer:
5'-TCAGTGGTACTTGTGGGACAGC-3'     (SEQ ID NO: 20)

α-fetoprotein [amplification size: 997 bp]
5'-primer:
5'-TGCTCAGTACGACAAGGTCG-3'       (SEQ ID NO: 21)

3'-primer:
5'-ACTGGTGATGCATAGCCTCC-3'       (SEQ ID NO: 22)

transthyretin [amplification size: 440 bp]
5'-primer:
5'-AGTCCTGGATGCTGTCCGAG-3'       (SEQ ID NO: 23)

3'-primer:
5'-TCAGAGGTCGGGCAGCCCAGC-3'      (SEQ ID NO: 24)
```

Figure 7:
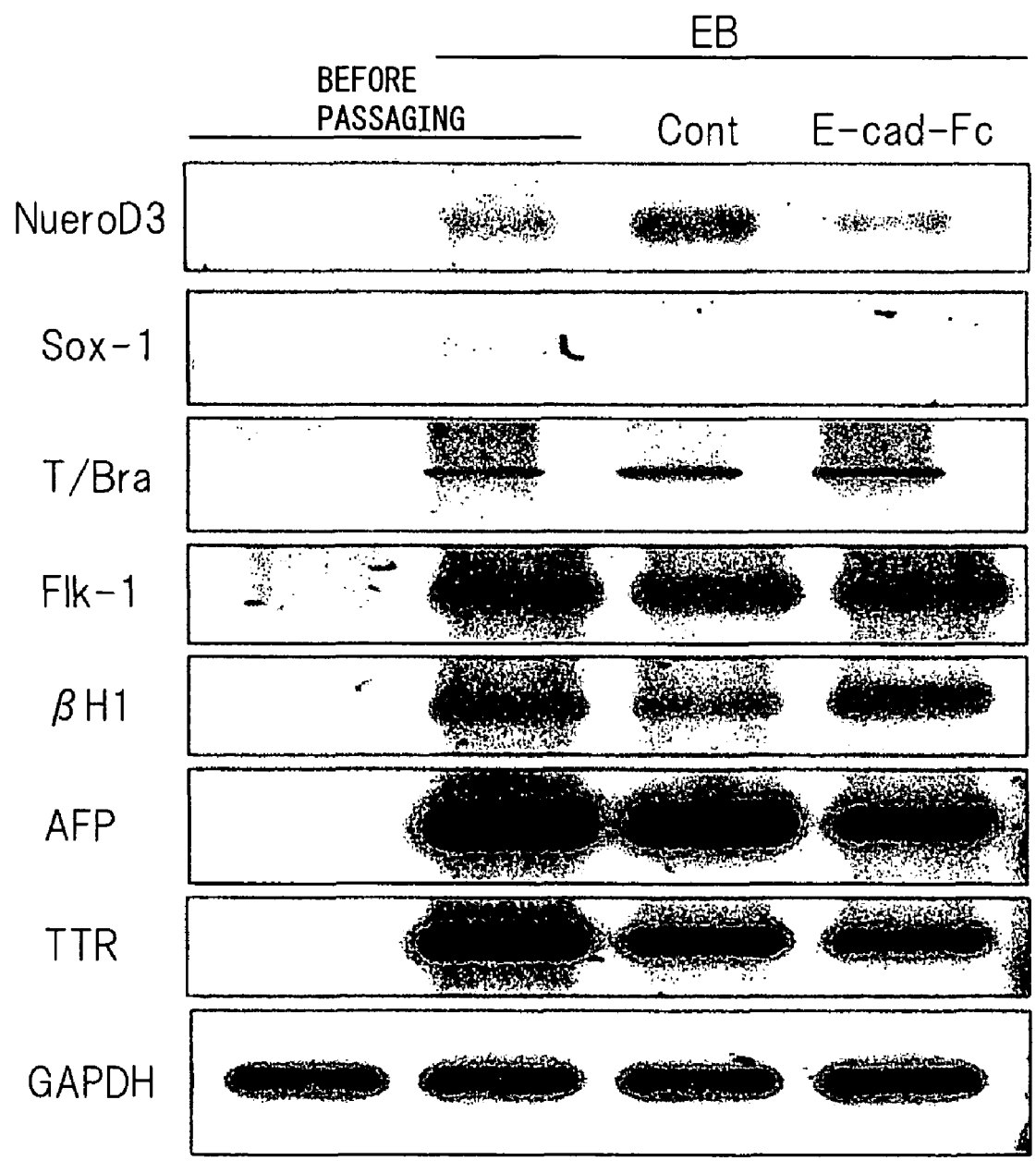
FIG. 7 is a set of photographs showing pluripotency of ES cells passaged on an E-cad-Fc plate. The ES cells (R1 line) seeded and passaged on a gelatin plate (indicated as Cont) or an E-cad-Fc plate were recovered, and an EB was formed in LIF-free medium to induce differentiation. Samples recovered on day 16 after EB formation ("EB" in the figure) were used for examination of different differentiation marker gene expressions by RT-PCR. As control groups there were used ES cells prior to the aforementioned passaging and the 16th day EB formed using those cells (1st and 2nd from left in the figure, respectively). T/Bra: T/Brachyury, βHl: hemoglobin, AFP: α-fetoprotein, TTR: transthyretin, GAPDH: glyceraldehyde-3-phosphate dehydrogenase.

The results are shown in FIG. 7. When LIF was removed from the medium to induce spontaneous differentiation of the EB from ES cells cultured on an ordinary gelatin plate, expression of specific marker genes of three germ layers including ectoderm (NeuroD3, Sox-1), mesoderm (T/Brachyury, Flk-1, hemoglobin) and endoderm (α-fetoprotein, transthyretin) was observed. Even with the ES cells cultured on an E-cad-Fc plate, expression of all three germ layer marker genes was confirmed at about the same level as the gelatin plate group.

The ability of the ES cells to differentiate to neurons and cardiomyocytes was then examined. It has been reported that co-culturing of ES cells with feeder cells that are stromal cells seeded beforehand on a culturing plate can induce their differentiation of ES cells to neurons and/or cardiomyocytes (Yamane et al., Methods Mol. Biol. 184:261, 2002; Schroeder et al., Proc. Natl. Acad. Sci. USA 100:4018, 2003). Thus, the ability of ES cells to differentiate to neurons was examined in a differentiation system using PA6 cells, and the ability to differentiate to cardiomyocytes was examined in a system using ST2 cells. PA6 cells or ST2 cells (both obtained from RIKEN Cell Bank) were seeded on a 6-well cell-culturing plate (CORNING) and cultured to confluency using DMEM (Invitrogen) medium containing 10% FBS, for use as feeder cells. Next, a culture medium of ES cells as single cells was prepared, and the feeder cells were rinsed twice with PBS and seeded at 2000 cells per well. On the following day, the culture medium was replaced with ESM containing 20% KnockOut Serum Replacement (Invitrogen) for the neural differentiation system (PA6 feeder), and with ESM containing 10% FBS for the cardiac differentiation system (ST2 feeder). The cells on day 12 of culturing were fixed with a 70% ethanol solution and reacted with anti-Microtubule-Associated Protein-2 (MAP-2) antibody (AB5622; Chemicon) or anti-sarcomere myosin antibody (MF20; American Type Culture Collection) as the primary antibody, and then with horseradish peroxidase-labeled secondary antibody (Histofine Simple Stain PO(R) or PO(M); Nichirei Biosciences), and finally color reaction was conducted using ACE (3-amino-9-ethylcarbazole) substrate solution (Nichirei Biosciences), after which observation was performed with an optical microscope. The results are shown in FIG. 8.

When ES cells cultured on an ordinary gelatin plate were seeded on PA6 cells under these culturing conditions, colonies formed to a size observable with the naked eye within a few days of culturing, and at around day 7 of culturing, a morphological change had occurred to differentiated cells exhibiting a distinct neurite structure. The cells were strongly positive for the neuron marker MAP-2, indicating that the ES cells had differentiated into neurons. The ES cells seeded on ST2 cells formed cell colonies exhibiting autonomous beating from day 12 of culturing, and the cell colonies were strongly positive for the cardiomyocyte marker sarcomere myosin, clearly indicating that the ES cells had differentiated into cardiomyocytes. Differentiation into neurons and cardiomyocytes was also confirmed when using the ES cells cultured on an E-cad-Fc plate, similar to the control group. These experimental results demonstrate that ES cells cultured on an E-cad-Fc plate retain their pluripotency in vitro.

The teratoma-forming ability of the ES cells was examined next. A teratoma is a tumor, comprising fetal and mature tissues from three germ layers of endoderm, mesoderm and ectoderm, which is formed when ES cells are transplanted into an animal such as a mouse, and teratoma-forming ability is used as an indicator of the pluripotency of ES cells.

ES cells (EB3 line) were seeded on a gelatin plate and an E-cad-Fc plate and passaged 5 times every three days. The ES cells were injected into Balb/c nude mouse testes (approximately 200 cells each) by an ordinary tests, and on day 60, teratoma formation was found in all of the ES cell-transplanted testes, with no noticeable difference in tumor size between the gelatin plate-cultured group and the E-cad-Fc plate-cultured group. Also, upon preparing tissue sections by a common method and observing the histology, the teratomas of both groups had ectodermal tissue/cell formation including epidermal-like tissue and neurons which were positive for different neuron markers (βIII-tubulin, GFAP, neurofilament M, GAP-43), mesodermal tissue/cell formation including bone, cartilage and skeletal muscle-like tissue and endodermal tissue/cells including intestinal and bronchoepithelial-like tissue, and therefore the ES cells cultured on E-cad-Fc plate were confirmed to have maintained teratoma-forming ability.

Example 5

Examination of Chimera-Forming Ability of ES Cells Cultured on E-cad-Fc Plate

It was determined whether ES cells passaged multiple times on an E-cad-Fc plate retain chimera-forming ability. ES cells (EB3 cell line) taken from the same cell lot of frozen stock confirmed to have chimera-forming ability were seeded on a gelatin plate and E-cad-Fc plate, and were passaged 5 times every three days. The ES cells were injected into C57BL/6 mouse blastocysts (approximately 100 cells each) by an ordinary method, and these were transplanted into the uteruses of pseudopregnant ICR mice (8-10 weeks old) and brought to parturition. C57BL/6 mice are normally black-haired, but some newborn individuals will have ES cell-derived agouti-colored hair on a portion of the body (5-80%); a total of four such chimeric mice were obtained from the ES cells cultured on a gelatin plate, and a total of seven were obtained from ES cells cultured on an E-cad-Fc plate.

Figure 9:
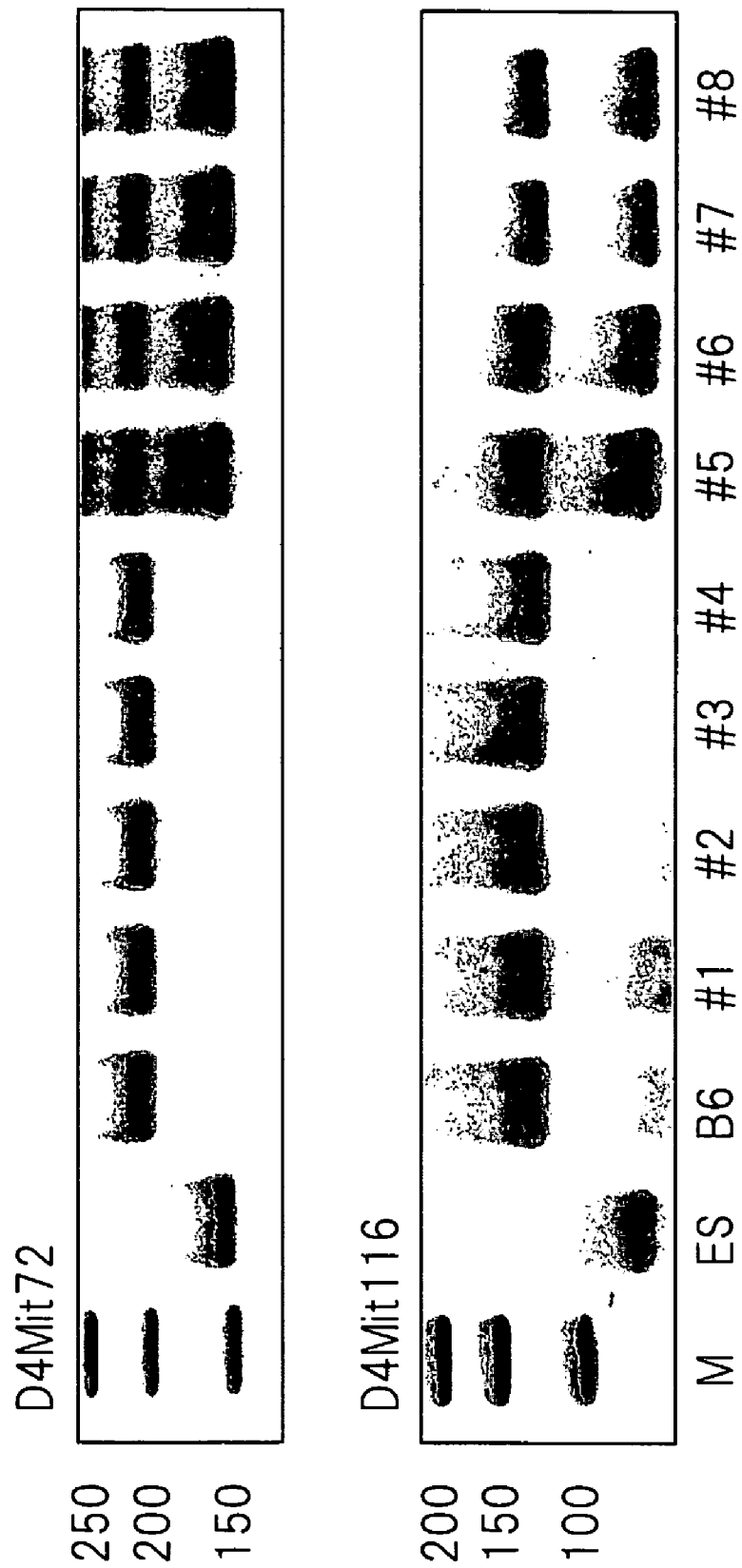
FIG. 9 is a pair of photographs showing germ-line transmission of ES cells cultured on an E-cad-Fc plate. A chimeric mouse generated from ES cells cultured on an E-cad-Fc plate was crossed with a wild-type C57BL/6 mouse, and the progeny mice were subjected to PCR analysis using two different microsatellite markers. M: DNA size marker, ES: ES cells (EB3 line), B6: C57BL/6 mouse, #1-#4: individuals thought to have no contribution of ES cells based on coat color, #5-#8: individuals thought to have contribution of ES cells based on coat color. The numbers on the vertical axis represent DNA size (bp).

The chimeric mice were then crossed with normal ICR mice to produce offspring to confirm that the ES cell-derived coat color was transmitted to the next generation. From two chimeric male mice generated by transplantation of ES cells cultured on an E-cad-Fc plate there were obtained 14 and 17 pups, respectively, of which 5 and 6, respectively, exhibited ES cell-derived coat color among individuals exhibiting the coat color of the C57BL/6 mice whose blastocysts were used as hosts. Analysis of mouse strain-specific microsatellite markers confirmed that these individuals had a genotype derived from the ES cells (FIG. 9). Specifically, genomic DNA was obtained from each young individual by a conventional method and the four microsatellite markers D4Mit72, D4Mit116, D7Mit276 and D10Mit186 were detected to allow genetic distinction between the 129SV mice derived from ES cells and the C57BL/6 mice used for chimeric mice generation and cross-breeding. As a result, in individuals thought to have no genetic contribution by ES cells based on coat color (#1-#4 in the photograph), the same pattern for all of the microsatellite markers was found as with C57BL/6 mice. On the other hand, in individuals thought to have genetic contribution by ES cells based on coat color (#5-#8 in the photograph), both the C57BL/6 mouse pattern and the ES cell-specific pattern was found, confirming that the ES cells genes had been transmitted to these individuals.

Example 6

Examination of Gene Transfer Rate in ES Cells Cultured on E-cad-Fc Plate

Figure 10:
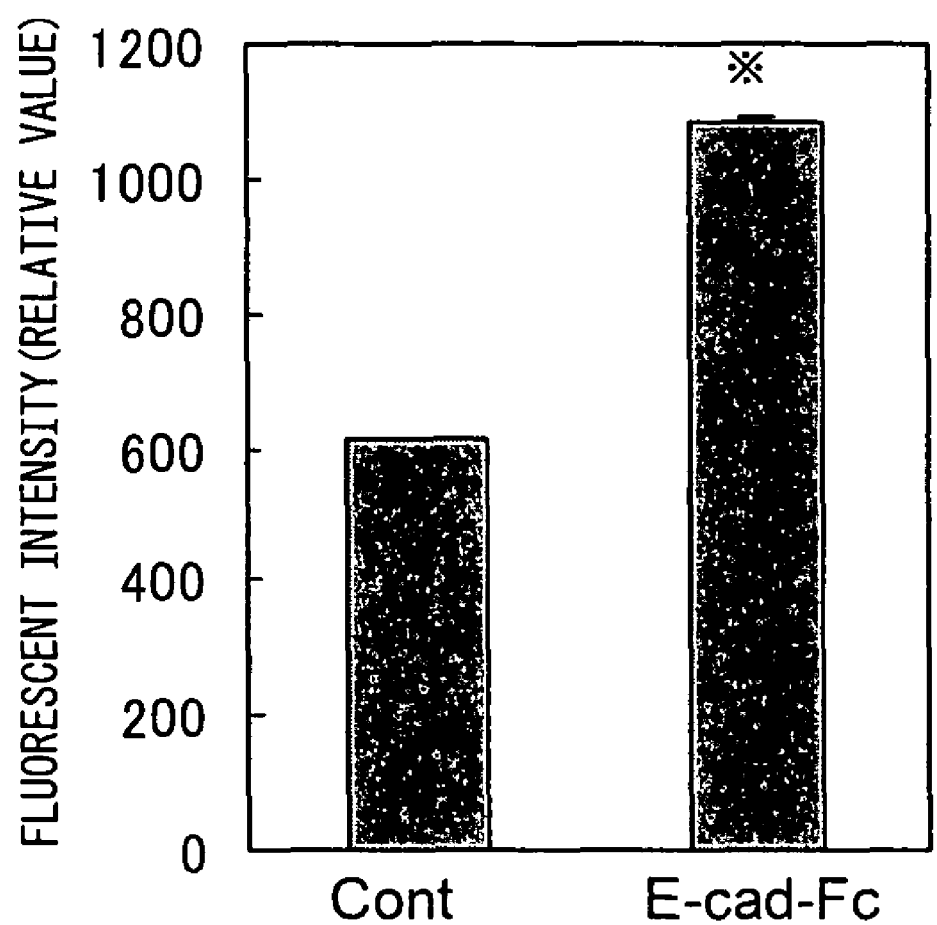
FIG. 10 is graph showing gene transfer/expression efficiency for ES cells seeded on an E-cad-Fc plate. The ES cells (EB3) were seeded on a gelatin plate (indicated as Cont) or an E-cad-Fc plate, and they were subjected to gene transfer with a GFP expression vector. The GFP in the cells after one day was detected by antibody stain using a fluorescent dye, and the fluorescent intensity was measured. *: with respect to Cont group, $p<0.01$.

A conventional method with Lipofectamine 2000 (Invitrogen) was used for transfer of the GFP expression vector pEGFP—N2 (Clontech) into ES cells that had been cultured for 3 days on a gelatin plate or E-cad-Fc plate. Single cells were recovered after one day, and were reseeded in a 96-well plate. After 4 hours, the adhered ES cells were fixed for 10 minutes with an 8% formalin solution, and they were then treated with a 0.2% Triton X-100/PBS solution and an Image-iT FX signal enhancer (Invitrogen). After rinsing with PBS and reaction with anti-GFP monoclonal antibody (Nacalai Tesque), dyeing was performed using Alexa Fluor 546-labeled anti-rat IgG antibody. The cell nuclei were stained with DAPI solution (0.1 μg/mL). The antibody and dye stain images were observed using an ArrayScan™ system (Cellomics). As a result, significantly higher expression of GFP was found in the E-cad-Fc plate-cultured group than in the ordinary plate-cultured group, showing that the E-cad-Fc plate-cultured ES cells had a higher gene transfer efficiency and/or expression efficiency than the ordinary-cultured ES cells (see FIG. 10).

Example 7

Preparation of Human E-cad-Fc Protein and Examination of Usability

In order to construct a vector expressing a fusion protein of the human E-cadherin extracellular region and IgG/Fc (hereinafter referred to as hE-cad-Fc), cDNA from the human squamous cell carcinoma line A431 was used as a template for amplification of a DNA fragment (corresponding to amino acid residues 1-697) coding for the extracellular domain of human E-cadherin (hE-cad-ECD). After confirming the nucleotide sequence, it was inserted into an expression vector containing the IgG/Fc sequence mentioned in Example 1 to construct pRC-hE-cad-Fc. Construction and purification of the vector hE-cad-Fc was accomplished according to the method described in Example 1.

Figure 11:
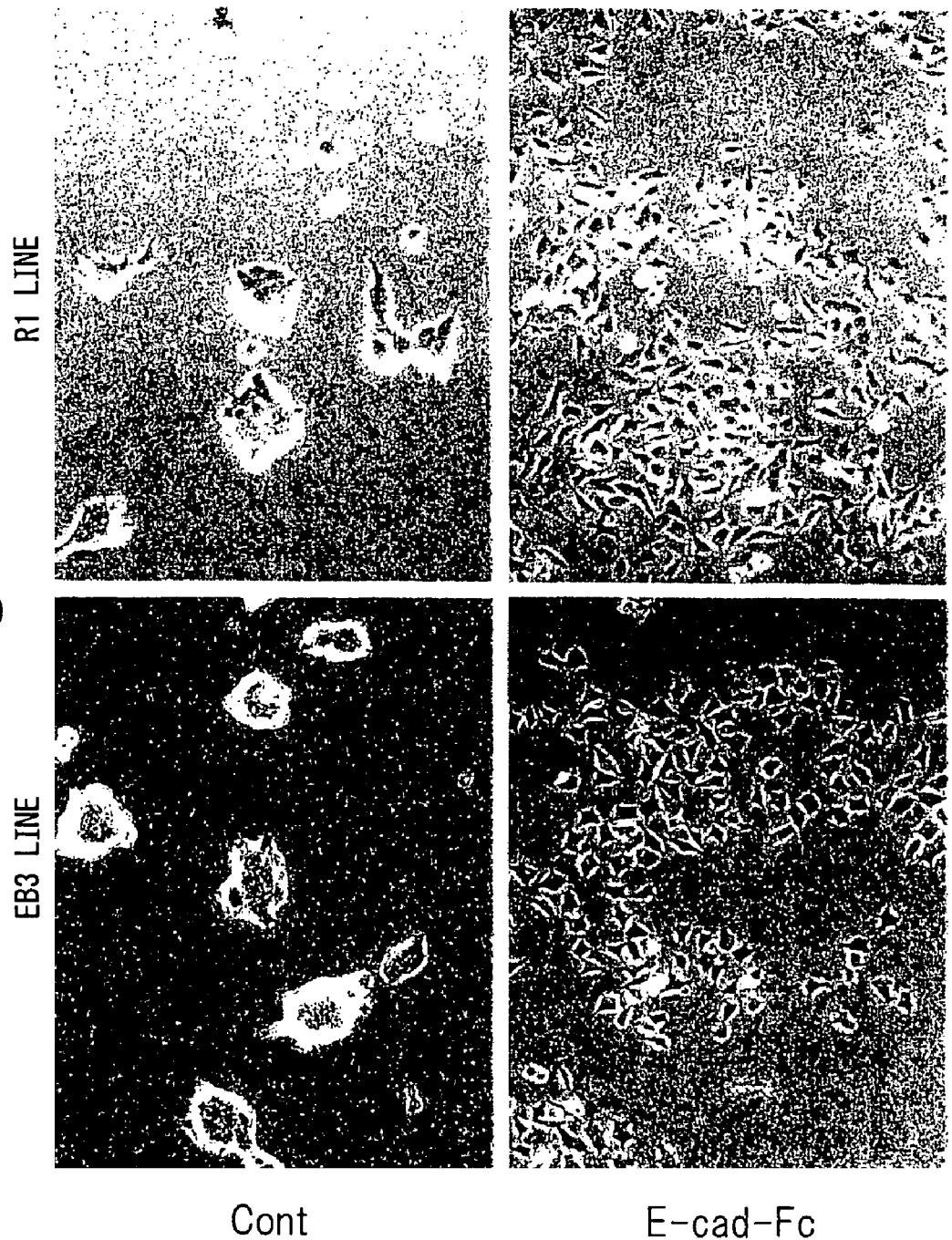
FIG. 11 is a set of photographs showing the morphology of ES cells seeded on a human E-cad-Fc plate. The cell images were taken two days after seeding the ES cells on a plate coated with gelatin (Cont) or E-cad-Fc.

Adhesion and proliferation of murine ES cells on cell culturing plates coated with the hE-cad-Fc protein (hereunder, "hE-cad-Fc plates") were examined. The method of preparing the hE-cad-Fc plates was the same as described in Example 2 above. Specifically, a PBS-diluted solution of the hE-cad-Fc protein was poured into untreated polystyrene culturing plates and treated for coating overnight at 37° C., for use as hE-cad-Fc plates. When ES cells (EB3 and R1 lines) were seeded in the plates, strong adhesion was exhibited as when using plates coated with murine E-cad-Fc protein. Also, the ES cells seeded in the hE-cad-Fc plates failed to form distinct colonies even 2 or 3 days after seeding, and the individual cells were observed to be in a dispersed and actively proliferating state (FIG. 11). The undifferentiated state and pluripotency of the ES cells were also maintained, as with culturing using murine E-cad-Fc plates.

By using the growing method of the invention, it is possible to produce pluripotent stem cells, such as ES cells, efficiently and on a large scale without using feeder cells. Moreover, since the pluripotent stem cells can be cultured in a dispersed state, passaging and cell recovery are greatly facilitated. It is also possible to reduce the amount of factors such as LIF that are added to liquid culturing medium. In addition, the method of the invention allows efficient transfer of desired genes into pluripotent stem cells such as ES cells, and allows high levels of expression thereof. The pluripotent stem cells produced in this manner can be utilized for production of various types of functionally differentiated cells by applying suitable known differentiation-inducing systems, and are useful for pharmacological evaluation or activity evaluation of various physiologically active substances or novel gene products of unknown function.

The invention claimed is:

1. A method for growing pluripotent stem cells which exhibit a normal karyotype comprising contacting said pluripotent stem cells with a liquid medium and growing said pluripotent stem cells in said liquid medium in a dispersed state in a culturing vessel without using feeder cells, wherein said pluripotent stem cells maintain their undifferentiated state and pluripotency, said culturing vessel including immobilized or coated on a substrate solid phase surface a cadherin molecule, and wherein said pluripotent stem cells achieve cell counts at least two times greater than said pluripotent stem cells cultured on a gelatin plate after four days.

2. The method of claim 1, further comprising transferring a gene into said pluripotent stem cells, after culturing.

3. The method of claim 1, wherein said cadherin molecule is E-cadherin, or a molecule which has structural homology with said molecule, which comprises the EC1 domain and one or more domains from among the EC2 domain, EC3 domain, EC4 domain and EC5 domain of E-cadherin, and which has homophilic binding ability with said pluripotent stem cells.

4. The method of claim 3, wherein said E-cadherin is mammalian.

5. The method of claim 4, wherein said E-cadherin is human or mouse.

6. The method of claim 1, wherein said cadherin molecule is fused with an immunoglobulin Fc region and is immobilized on said substrate solid phase surface via said Fc region.

7. The method of claim 1, wherein said pluripotent stem cells are mammalian embryonic stem cells (ES cells) or embryonic germ cells (EG cells).

8. The method of claim 2, wherein said cadherin molecule is E-cadherin, or a molecule which has structure homology with said molecule, which comprises the EC1 domain and one or more domains from the EC2 domain, EC3 domain, EC4 domain and EC5 domain of E-cadherin, and which has homophilic binding ability with said pluripotent stem cells.

9. The method of claim 8, wherein said E-cadherin is mammalian.

10. The method of claim 9, wherein said E-cadherin is human or mouse.

11. The method of claim 2, wherein said cadherin molecule is fused with an immunoglobulin Fc region and is immobilized on said substrate solid phase surface via said Fc region.

12. The method of claim 2, wherein said pluripotent stem cells are mammalian embryonic stem cells (ES cells) or embryonic germ cells (EG cells).

13. The method of claim 2, wherein said cadherin molecule is a human or a mouse E-cadherin and said pluripotent stem cells are mammalian embryonic stem cells (ES cells).

* * * * *

```
                        SEQUENCE LISTING

<160> NUMBER OF SEQ ID NOS: 24

<210> SEQ ID NO 1
<211> LENGTH: 882
<212> TYPE: PRT
<213> ORGANISM: Human E-cadherin
<220> FEATURE:
<221> NAME/KEY: DOMAIN
<222> LOCATION: (157)..(262)
<223> OTHER INFORMATION: EC1
<220> FEATURE:
<221> NAME/KEY: DOMAIN
<222> LOCATION: (265)..(375)
<223> OTHER INFORMATION: EC2
<220> FEATURE:
<221> NAME/KEY: DOMAIN
<222> LOCATION: (378)..(486)
<223> OTHER INFORMATION: EC3
<220> FEATURE:
<221> NAME/KEY: DOMAIN
<222> LOCATION: (487)..(595)
<223> OTHER INFORMATION: EC4
<220> FEATURE:
<221> NAME/KEY: DOMAIN
<222> LOCATION: (596)..(700)
<223> OTHER INFORMATION: EC5

<400> SEQUENCE: 1

Met Gly Pro Trp Ser Arg Ser Leu Ser Ala Leu Leu Leu Leu Leu Gln
1               5                   10                  15
```

-continued

```
Val Ser Ser Trp Leu Cys Gln Glu Pro Glu Pro Cys His Pro Gly Phe
             20                  25                  30

Asp Ala Glu Ser Tyr Thr Phe Thr Val Pro Arg Arg His Leu Glu Arg
             35                  40                  45

Gly Arg Val Leu Gly Arg Val Asn Phe Glu Asp Cys Thr Gly Arg Gln
 50                  55                  60

Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
             85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
            115                 120                 125

Gln Ala Ser Val Ser Gly Ile Gln Ala Glu Leu Leu Thr Phe Pro Asn
130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
            195                 200                 205

Arg Glu Thr Gly Trp Leu Lys Val Thr Glu Pro Leu Asp Arg Glu Arg
210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
```

-continued

```
                435                 440                 445
Gln Tyr Ile Leu His Val Ala Val Thr Asn Val Pro Phe Glu Val
450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
            755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
850                 855                 860
```

```
Trp Gly Asn Arg Phe Lys Lys Leu Ala Asp Met Tyr Gly Gly Gly Glu
865                 870                 875                 880

Asp Asp

<210> SEQ ID NO 2
<211> LENGTH: 884
<212> TYPE: PRT
<213> ORGANISM: Mouse E-cadherin
<220> FEATURE:
<221> NAME/KEY: DOMAIN
<222> LOCATION: (159)..(264)
<223> OTHER INFORMATION: EC1
<220> FEATURE:
<221> NAME/KEY: DOMAIN
<222> LOCATION: (267)..(377)
<223> OTHER INFORMATION: EC2
<220> FEATURE:
<221> NAME/KEY: DOMAIN
<222> LOCATION: (380)..(488)
<223> OTHER INFORMATION: EC3
<220> FEATURE:
<221> NAME/KEY: DOMAIN
<222> LOCATION: (489)..(597)
<223> OTHER INFORMATION: EC4
<220> FEATURE:
<221> NAME/KEY: DOMAIN
<222> LOCATION: (598)..(702)
<223> OTHER INFORMATION: EC5

<400> SEQUENCE: 2

Met Gly Ala Arg Cys Arg Ser Phe Ser Ala Leu Leu Leu Leu Leu Gln
1               5                   10                  15

Val Ser Ser Trp Leu Cys Gln Glu Leu Glu Pro Glu Ser Cys Ser Pro
            20                  25                  30

Gly Phe Ser Ser Glu Val Tyr Thr Phe Pro Val Pro Glu Arg His Leu
        35                  40                  45

Glu Arg Gly His Val Leu Gly Arg Val Arg Phe Glu Gly Cys Thr Gly
    50                  55                  60

Arg Pro Arg Thr Ala Phe Phe Ser Glu Asp Ser Arg Phe Lys Val Ala
65                  70                  75                  80

Thr Asp Gly Thr Ile Thr Val Lys Arg His Leu Lys Leu His Lys Leu
                85                  90                  95

Glu Thr Ser Phe Leu Val Arg Ala Arg Asp Ser Ser His Arg Glu Leu
            100                 105                 110

Ser Thr Lys Val Thr Leu Lys Ser Met Gly His His His Arg His
        115                 120                 125

His His Arg Asp Pro Ala Ser Glu Ser Asn Pro Glu Leu Leu Met Phe
    130                 135                 140

Pro Ser Val Tyr Pro Gly Leu Arg Arg Gln Lys Arg Asp Trp Val Ile
145                 150                 155                 160

Pro Pro Ile Ser Cys Pro Glu Asn Glu Lys Gly Glu Phe Pro Lys Asn
                165                 170                 175

Leu Val Gln Ile Lys Ser Asn Arg Asp Lys Glu Thr Lys Val Phe Tyr
            180                 185                 190

Ser Ile Thr Gly Gln Gly Ala Asp Lys Pro Pro Val Gly Val Phe Ile
        195                 200                 205

Ile Glu Arg Glu Thr Gly Trp Leu Lys Val Thr Gln Pro Leu Asp Arg
    210                 215                 220

Glu Ala Ile Ala Lys Tyr Ile Leu Tyr Ser His Ala Val Ser Ser Asn
225                 230                 235                 240
```

```
Gly Glu Ala Val Glu Asp Pro Met Glu Ile Val Ile Thr Val Thr Asp
            245                 250                 255
Gln Asn Asp Asn Arg Pro Glu Phe Thr Gln Pro Val Phe Glu Gly Phe
            260                 265                 270
Val Ala Glu Gly Ala Val Pro Gly Thr Ser Val Met Lys Val Ser Ala
            275                 280                 285
Thr Asp Ala Asp Asp Val Asn Thr Tyr Asn Ala Ala Ile Ala Tyr
            290                 295                 300
Thr Ile Val Ser Gln Asp Pro Glu Leu Pro His Lys Asn Met Phe Thr
305                 310                 315                 320
Val Asn Arg Asp Thr Gly Val Ile Ser Val Leu Thr Ser Gly Leu Asp
                325                 330                 335
Arg Glu Ser Tyr Pro Thr Tyr Thr Leu Val Val Gln Ala Ala Asp Leu
                340                 345                 350
Gln Gly Glu Gly Leu Ser Thr Thr Ala Lys Ala Val Ile Thr Val Lys
                355                 360                 365
Asp Ile Asn Asp Asn Ala Pro Val Phe Asn Pro Ser Thr Tyr Gln Gly
370                 375                 380
Gln Val Pro Glu Asn Glu Val Asn Ala Arg Ile Ala Thr Leu Lys Val
385                 390                 395                 400
Thr Asp Asp Asp Ala Pro Asn Thr Pro Ala Trp Lys Ala Val Tyr Thr
                405                 410                 415
Val Val Asn Asp Pro Asp Gln Gln Phe Val Val Thr Asp Pro Thr
                420                 425                 430
Thr Asn Asp Gly Ile Leu Lys Thr Ala Lys Gly Leu Asp Phe Glu Ala
                435                 440                 445
Lys Gln Gln Tyr Ile Leu His Val Arg Val Glu Asn Glu Glu Pro Phe
450                 455                 460
Glu Gly Ser Leu Val Pro Ser Thr Ala Thr Val Thr Val Asp Val Val
465                 470                 475                 480
Asp Val Asn Glu Ala Pro Ile Phe Met Pro Ala Glu Arg Arg Val Glu
                485                 490                 495
Val Pro Glu Asp Phe Gly Val Gly Gln Glu Ile Thr Ser Tyr Thr Ala
                500                 505                 510
Arg Glu Pro Asp Thr Phe Met Asp Gln Lys Ile Thr Tyr Arg Ile Trp
                515                 520                 525
Arg Asp Thr Ala Asn Trp Leu Glu Ile Asn Pro Glu Thr Gly Ala Ile
530                 535                 540
Phe Thr Arg Ala Glu Met Asp Arg Glu Asp Ala Glu His Val Lys Asn
545                 550                 555                 560
Ser Thr Tyr Val Ala Leu Ile Ile Ala Thr Asp Asp Gly Ser Pro Ile
                565                 570                 575
Ala Thr Gly Thr Gly Thr Leu Leu Leu Val Leu Leu Asp Val Asn Asp
                580                 585                 590
Asn Ala Pro Ile Pro Glu Pro Arg Asn Met Gln Phe Cys Gln Arg Asn
                595                 600                 605
Pro Gln Pro His Ile Ile Thr Ile Leu Asp Pro Asp Leu Pro Pro Asn
                610                 615                 620
Thr Ser Pro Phe Thr Ala Glu Leu Thr His Gly Ala Ser Val Asn Trp
625                 630                 635                 640
Thr Ile Glu Tyr Asn Asp Ala Ala Gln Glu Ser Leu Ile Leu Gln Pro
                645                 650                 655
Arg Lys Asp Leu Glu Ile Gly Glu Tyr Lys Ile His Leu Lys Leu Ala
```

```
                        660             665             670
Asp Asn Gln Asn Lys Asp Gln Val Thr Thr Leu Asp Val His Val Cys
            675                 680                 685

Asp Cys Glu Gly Thr Val Asn Asn Cys Met Lys Ala Gly Ile Val Ala
        690                 695                 700

Ala Gly Leu Gln Val Pro Ala Ile Gly Ile Gly Gly Ile Leu
705                 710                 715                 720

Ala Leu Leu Ile Leu Ile Leu Leu Leu Leu Phe Leu Arg Arg Arg
                725                 730                 735

Thr Val Val Lys Glu Pro Leu Leu Pro Pro Asp Asp Thr Arg Asp
                740                 745                 750

Asn Val Tyr Tyr Tyr Asp Glu Glu Gly Gly Gly Glu Glu Asp Gln Asp
                755                 760                 765

Phe Asp Leu Ser Gln Leu His Arg Gly Leu Asp Ala Arg Pro Glu Val
            770                 775                 780

Thr Arg Asn Asp Val Ala Pro Thr Leu Met Ser Val Pro Gln Tyr Arg
785                 790                 795                 800

Pro Arg Pro Ala Asn Pro Asp Glu Ile Gly Asn Phe Ile Asp Glu Asn
                805                 810                 815

Leu Lys Ala Ala Asp Ser Asp Pro Thr Ala Pro Pro Tyr Asp Ser Leu
                820                 825                 830

Leu Val Phe Asp Tyr Glu Gly Ser Gly Ser Glu Ala Ala Ser Leu Ser
            835                 840                 845

Ser Leu Asn Ser Ser Glu Ser Asp Gln Asp Gln Asp Tyr Asp Tyr Leu
        850                 855                 860

Asn Glu Trp Gly Asn Arg Phe Lys Lys Leu Ala Asp Met Tyr Gly Gly
865                 870                 875                 880

Gly Glu Asp Asp

<210> SEQ ID NO 3
<211> LENGTH: 21
<212> TYPE: DNA
<213> ORGANISM: Oct-3/4,size 528 bp, 5'primer

<400> SEQUENCE: 3
gaagttggag aaggtggaac c                                        21

<210> SEQ ID NO 4
<211> LENGTH: 21
<212> TYPE: DNA
<213> ORGANISM: Oct-3/4,size 528 bp, 3'primer

<400> SEQUENCE: 4
gcctcatact cttctcgttg g                                        21

<210> SEQ ID NO 5
<211> LENGTH: 20
<212> TYPE: DNA
<213> ORGANISM: Rex1,size 930 bp, 5'primer

<400> SEQUENCE: 5
aaagtgagat tagccccgag                                          20

<210> SEQ ID NO 6
<211> LENGTH: 20
<212> TYPE: DNA
<213> ORGANISM: Rex1,size 930 bp, 3'primer
```

```
<400> SEQUENCE: 6
tcccatcccc ttcaatagca                                          20

<210> SEQ ID NO 7
<211> LENGTH: 20
<212> TYPE: DNA
<213> ORGANISM: Nanog,size 930 bp, 5'primer

<400> SEQUENCE: 7
gaggaagcat cgaattctgg                                          20

<210> SEQ ID NO 8
<211> LENGTH: 20
<212> TYPE: DNA
<213> ORGANISM: Nanog, size 930 bp, 3'primer

<400> SEQUENCE: 8
aagttatgga gcggagcagc                                          20

<210> SEQ ID NO 9
<211> LENGTH: 19
<212> TYPE: DNA
<213> ORGANISM: GAPDH,size 858 bp, 5'primer

<400> SEQUENCE: 9
ggaagcttgt catcaacgg                                           19

<210> SEQ ID NO 10
<211> LENGTH: 20
<212> TYPE: DNA
<213> ORGANISM: GAPDH, size 858 bp, 3'primer

<400> SEQUENCE: 10
ctcttgctca gtgtccttgc                                          20

<210> SEQ ID NO 11
<211> LENGTH: 19
<212> TYPE: DNA
<213> ORGANISM: NeuroD3, size 405 bp, 5'primer

<400> SEQUENCE: 11
catctctgat ctcgactgc                                           19

<210> SEQ ID NO 12
<211> LENGTH: 19
<212> TYPE: DNA
<213> ORGANISM: NeuroD3, size 405 bp, 3'primer

<400> SEQUENCE: 12
ccagatgtag ttgtaggcg                                           19

<210> SEQ ID NO 13
<211> LENGTH: 19
<212> TYPE: DNA
<213> ORGANISM: Sox1, size 407 bp, 5'primer

<400> SEQUENCE: 13
gcacacagcg ttttctcgg                                           19

<210> SEQ ID NO 14
<211> LENGTH: 19
<212> TYPE: DNA
<213> ORGANISM: Sox1, size 407 bp, 3'primer
```

```
<400> SEQUENCE: 14
acatccgact cctcttccc                                              19

<210> SEQ ID NO 15
<211> LENGTH: 20
<212> TYPE: DNA
<213> ORGANISM: T/Brachyury, size 528 bp, 5'primer

<400> SEQUENCE: 15
tccaggtgct atatattgcc                                             20

<210> SEQ ID NO 16
<211> LENGTH: 20
<212> TYPE: DNA
<213> ORGANISM: T/Brachyury, size 528 bp, 3'primer

<400> SEQUENCE: 16
tgctgcctgt gagtcacaac                                             20

<210> SEQ ID NO 17
<211> LENGTH: 22
<212> TYPE: DNA
<213> ORGANISM: Flk1, size 398 bp, 5'primer

<400> SEQUENCE: 17
taggtgcctc cccatacccT gg                                          22

<210> SEQ ID NO 18
<211> LENGTH: 22
<212> TYPE: DNA
<213> ORGANISM: Flk1, size 398 bp, 3'primer

<400> SEQUENCE: 18
tggccggctc tttcgcttac tg                                          22

<210> SEQ ID NO 19
<211> LENGTH: 19
<212> TYPE: DNA
<213> ORGANISM: beta-H1, size 415 bp, 5'primer

<400> SEQUENCE: 19
aaccctcaat ggcctgtgg                                              19

<210> SEQ ID NO 20
<211> LENGTH: 22
<212> TYPE: DNA
<213> ORGANISM: beta-H1, size 415 bp, 3'primer

<400> SEQUENCE: 20
tcagtggtac ttgtgggaca gc                                          22

<210> SEQ ID NO 21
<211> LENGTH: 20
<212> TYPE: DNA
<213> ORGANISM: alpha-fetoprotein, size 997 bp, 5'primer

<400> SEQUENCE: 21
tgctcagtac gacaaggtcg                                             20

<210> SEQ ID NO 22
<211> LENGTH: 20
<212> TYPE: DNA
```

```
<213> ORGANISM: alpha-fetoprotein, size 997 bp, 3'primer

<400> SEQUENCE: 22
actggtgatg catagcctcc                                              20

<210> SEQ ID NO 23
<211> LENGTH: 20
<212> TYPE: DNA
<213> ORGANISM: transthyretin, size 440 bp, 5'primer

<400> SEQUENCE: 23
agtcctggat gctgtccgag                                              20

<210> SEQ ID NO 24
<211> LENGTH: 21
<212> TYPE: DNA
<213> ORGANISM: transthyretin, size 440 bp, 3'primer

<400> SEQUENCE: 24
tcagaggtcg ggcagcccag c                                            21
```